United States Patent [19]

Callahan et al.

[11] Patent Number: 5,438,118
[45] Date of Patent: Aug. 1, 1995

[54] HIV PROTEASE INHIBITORS

[75] Inventors: James F. Callahan, Philadelphia; William F. Huffman, Malvern; Michael L. Moore, Media; Kenneth A. Newlander, West Chester, all of Pa.

[73] Assignee: SmithKline Beechman Corp., Philadelphia, Pa.

[21] Appl. No.: 66,136

[22] PCT Filed: Nov. 25, 1991

[86] PCT No.: PCT/US91/08850

§ 371 Date: Jul. 26, 1993

§ 102(e) Date: Jul. 26, 1993

[87] PCT Pub. No.: WO92/09297

PCT Pub. Date: Jun. 11, 1992

Related U.S. Application Data

[63] Continuation-in-part of Ser. No. 620,978, Nov. 30, 1990, abandoned.

[51] Int. Cl.⁶ .......... A61K 38/00; C07K 5/00; C07K 7/00; C07K 17/00
[52] U.S. Cl. .................. 530/330; 530/331; 540/492; 540/526; 540/531
[58] Field of Search .......... 514/17–19, 514/282, 218; 530/330, 331; 540/492, 526, 531

[56] References Cited

FOREIGN PATENT DOCUMENTS 352000 1/1990 European Pat. Off. .

OTHER PUBLICATIONS

Huffman et al. Proc. of the 10th American Peptide Symposium, issued 5/87 pp. 105–108.
ASM News 7/90, vol. 56 p. 368.
Blumenstein et al. Biochem Biophys. Res. Comm. vol. 163 p. 980 (1989).
Bolis et al. J. Med Chem. vol. 30 p. 1730 (1987).
Burger, Med. Chem. (1960) p. 565.

*Primary Examiner*—Jill Warden
*Assistant Examiner*—Sheela J. Huff
*Attorney, Agent, or Firm*—Charles M. Kinzig; Stephen Venetianer; Edward T. Lentz

[57] ABSTRACT

Peptide mimics, having a constrained peptide backbone conformation, are HIV protease inhibitors. A compound of this invention is, for example, 3-Benzyl-5(alaninyl-1-aminoethyl)-2,3,6,7-tetrahydro-N-azepinyl-2-propionyl-valinyl-valinyl methyl ester.

10 Claims, No Drawings

HIV PROTEASE INHIBITORS

This application is a continuation-in-part of application Ser. No. 07/620,978, filed Nov. 30, 1990, now abandoned.

The present invention is directed to compounds containing chemical mimics which constrain peptide conformation. These compounds are inhibitors of the human immunodeficiency virus (HIV) protease and are useful for treating HIV infection and for treating acquired immune deficiency syndrome (AIDS).

The compounds of this invention are also renin inhibitors and thus are useful in treating hypertension.

This invention further relates to pharmaceutical compositions which comprise a compound of this invention and a pharmaceutically acceptable carrier.

Also, this invention relates to methods of treating AIDS and to methods of preventing and/or treating infection by HIV. These methods comprise administering to a mammal in need thereof an effective amount of a compound of this invention.

BACKGROUND OF THE INVENTION

The retrovirus, HIV which is a virus within the family of Retroviridae, is the etiological agent of AIDS and AIDS-related complexes. Viral replication occurs only within host cells and is dependent upon host cellular functions. The production of functional viral proteins is critical to this replication. Protein synthesis is accomplished by translation of the open reading frames into polyprotein constructs, corresponding to the gag, pol, and env reading frames, which are processed, at least in part, by a viral protease into the functional proteins. The proteolytic activity provided by the viral protease in processing the polyproteins cannot be provided by the host and is essential to the life cycle of the retrovirus. Methods to express retroviral proteases in *E. coli* have been disclosed by Debouck, et al., *Proc. Natl. Acad. Sci. USA*, 8903–06 9 (1987) and Graves, et al., *Proc. Natl. Acad. Sci. USA*, 85, 2449–53 (1988) for the HIV-1 virus. In fact, it has been demonstrated that retroviruses which lack the protease, or contain a mutated form of it, lack infectivity. See Katoh et al., *Virology*, 145, 280-92 (1985), Crawford et al., *J. Virol*, 53, 899–907 (1985) and Debouck et al., *Proc. Natl. Acad. Sci. USA*, 84, 8903-6 (1987). Inhibition of retroviral proteases, such as HIV protease, presents a method of therapy for retroviral diseases, such as AIDS. There exists a need for compounds which inhibit retroviral protease activity for pharmaceutical use to provide therapy for diseases which are caused by such retroviruses.

EP-A 352,000 and EP-A 337,714, which are incorporated herein by reference, disclose peptide-like compounds which inhibit retroviral proteases. Neither of these references disclose compounds having the constrained peptide backbone conformation which is the significant feature of the inhibitor compounds of the present invention.

Gamma turn mimics have been reported in the following publications: Huffman et al., Peptides, Chemistry and Biology, Proceedings of the Tenth American Peptide Symposium, (Marshall, G., ed.), ESCOM, Luden, 1988, pp. 105-8. Huffman et al., Synthetic Peptides: Approaches to Biological Problems. UCLA Symposium on Molecular and Cellular Biology, Vol. 86 (Tam, J. and Kaiser, E., eds.) Alan R. Liss, Inc., New York, 1988. Huffman et al., 10th American Peptide Symposium, Abstract, May 1987. Callahan et al., 30th Organic Symposium, Abstract, June 1987. Lack of significant biological activity was reported.

X-ray crystal structures of certain aspartic acid-based enzyme inhibitors bound to the active sites of the enzymes reveal that a C-7 or gamma turn conformation about the amino acid in the P1 site is compatible with the pharmacophore for inhibition. We have found that compounds containing synthetic mimics, which constrain the peptide backbone conformation, are inhibitors of HIV protease. They are also inhibitors of renin.

DESCRIPTION OF THE INVENTION

The compounds of this invention are illustrated by the following Formula I:

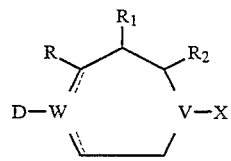

in which:

D is A' or

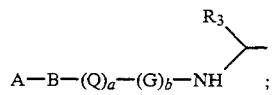

X is

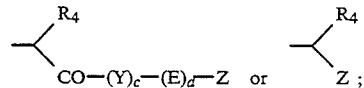

V and W are each independently N or C;

one of -- indicated bonds is a double bond and the other is a single bond or, when W is N, -- both are single bonds;

R is hydrogen or OH, or when W is N, R is $=O$;

$R_1$ is $C_{1-6}$ alkyl, $(CH_2)_n$ Ar, $(CH_2)_n$ Het, $(CH_2)_n CONHR'$, $(CH_2)_n$ OR' or $(CH_2)_n$ SR';

$R_2$ is:
 a) 2H, when V is N;
 b) OH, OR', $=CHR'$ or NHR', when V is C;
 c) $=O$, when V is N, D is

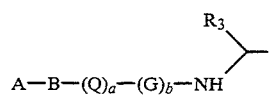

and X is

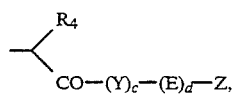

or when W and V are both N;

A' is hydrogen, $C_{1-6}$ alkyl, benzyl, halobenzyl, dihalobenzyl or tosyl;

A is hydrogen or an amino protecting group;

B is a D or L amino acid or is a covalent bond;

Q is a D or L amino acid selected for Ser, Thr, Asp, His, Cys, Arg and Ala;

G is Glx, Asx, Ala, β-Ala, Arg, Gly, Ile, Leu, Lys, Ser, Thr, Val, Met or His;

Y and E are each independently a D or L amino acid;

a, b, c and d are each independently 0 or 1;

Z is hydrogen $(CH_2)_nOR'$, $(CH_2)_nNHR'$, $C_{1-6}$alkyl, $(CH_2)_nSR'$, $O(CH_2)_pOR'$, $NH(CH_2)_pOR'$, $O(CH_2)_pSR'$ or $NH(CH_2)_pSR'$;

$R_3$ and $R_4$ are each independently hydrogen, $C_{1-6}$alkyl, $(CH_2)_n$Het, $(CH_2)_n$Ar, $(CH_2)_n$CONHR', $(CH_2)_nOR'$, $(CH_2)_nSR'$, $(CH_2)_nNHR'$, $CH(OH)CH_3$ or $(CH_2)_3NHC(=NH)NH_2$;

R' is hydrogen, $C_{1-4}$alkyl or benzyl;

n is 0 to 3;

p is 1 to 3;

Het is indolyl or imidazolyl, or pyridyl or thienyl optionally substituted by one or two $C_{1-4}$alkyl, OR' or SR'; and Ar is phenyl optionally substituted by one or two $C_{1-4}$alkyl, OR', $NO_2$, $NH_2$, halogen $CF_3$ or SR'; or a pharmaceutically acceptable salt thereof.

In Formula I, D is preferably

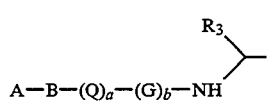

and also, X is preferably

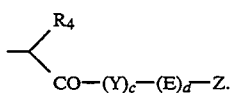

Also included in this invention are pharmaceutically acceptable addition salts, complexes or prodrugs of the compounds of this invention. Prodrugs are considered to be any covalently bonded carriers which release the active parent drug according to Formula I in vivo.

It should be noted that, in Formula I, A comprises the moiety (1) on the amino group when a and b are 0 and S is a covalent bond, (2) on the amino group of the amino acid of B when B is an amino acid, (3) on the amino group of the amino acid of Q when B is a covalent bond and a is 1, or (4) on the amino group of the amino acid of G when B is a covalent bond and a is 0. Z represents the terminal moiety on the carbonyl group when X is $CH(R_4)C(=O)—(Y)_c—(E)_d—Z$ and c and d are 0; or on the carbonyl group of the amino acid of Y when c is 1 and d is 0; or on the carbonyl group of the amino acid of E when d is 1.

In Formula I, the amino protecting group in the definition of A may be t-butyloxycarbonyl (Boc), benzyloxycarbonyl (Cbz), p-chlorobenzyloxycarbonyl (ClZ), 2,4-dichlorobenzyloxycarbonyl (Cl2Z), alkanoyl such as acetyl (Ac), or tosyl (Tos). Other amino protecting groups known to the art may also be used.

A subgeneric group of compounds of Formula I are reduced amides of the following Formula II:

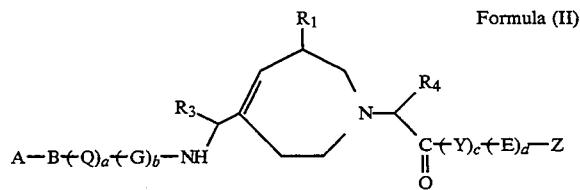

in which $R_1$, A, B, Q, G, Y, E, a, b, c, d, $R_3$, $R_4$ and Z are as defined in Formula I.

Another subgeneric group of compounds of Formula I are hydroxyethylene compounds which are represented by the following Formula III:

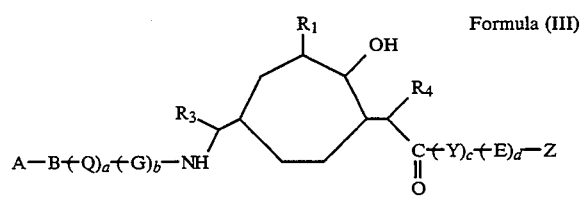

in which $R_1$, A, B, Q, G, Y, E, a, b, c, d, $R_3$, $R_4$ and Z are as defined in Formula I.

Further subgeneric groups of compounds of Formula I are represented by the following Formulas IV, V and VI:

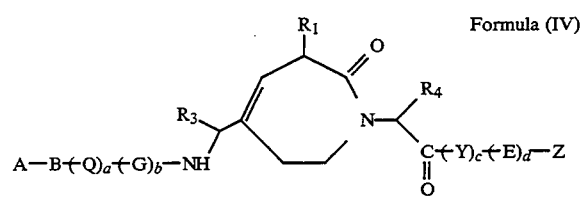

in which $R_2$ is =O; and $R_1$, A, B, Q, G, Y, E, d, $R_3$, $R_4$ and Z are as defined in Formula I;

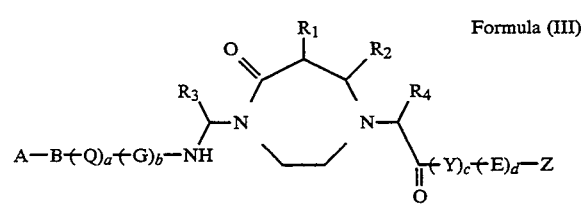

in which $R_2$ is 2H or =O; and $R_1$, A, B, Q, G, Y, E, a, b, c, d, $R_3$, $R_4$ and Z are as defined in Formula I; and

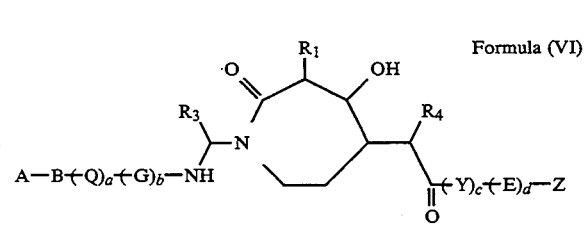

in which $R_1$, A, B, Q, G, Y, E, a, b, c, d, $R_3$, $R_4$ and Z are as defined in Formula I.

Abbreviations and symbols commonly used in the peptide art are used herein:

| Amino Acid (Residue) | Code | Amino Acid (Residue) |
|---|---|---|
| Alanine | Ala | |
| | Leu | Leucine |
| Arginine | Arg | |
| | Lys | Lysine |
| Asparagine | Asn | |
| | Met | Methionine |
| Aspartic Acid | Asp | |
| | Phe | Phenylalanine |
| Cysteine | Cys | |
| | Pro | Proline |
| Glutamine | Gln | |
| | Ser | Serine |
| Glutamic Acid | Glu | |
| | Thr | Threonine |
| Glycine | Gly | |
| | Trp | Tryptophan |
| Histidine | His | |
| | Tyr | Tyrosine |
| Isoleucine | Ile | |
| | Val | Valine |
| Asparagine or Aspartic Acid | Asx | |
| Glutamine or Glutamic Acid | Glx | |

In accordance with conventional representation, the amino terminus is on the left and the carboxy terminus is on the right. Unless specified otherwise, all chiral amino acids are assumed to be of the L absolute configuration. β-Ala refers to 3-amino propanoic acid, Bzl refers to benzyl, Cbz refers to the carbobenzyloxy radical, DCC refers to dicyclohexylcarbodiimide, DMAP refers to N,N-dimethylaminopyridine, HOBt refers to 1-hydroxy-benzotriazole, NMM is N-methylmorpholine, DMA is dimethylacetamide, DMF is dimethyl formamide, THF is tetrahydrofuran and TFA refers to trifluoroacetic acid. Also, BnOH or Bzl-OH is benzyl alcohol, TBDMS-Cl is t-butyldimethylsilyl chloride, DPPA is diphenylphosphoryl azide. As used herein in the compounds of this invention, Asp and Glu, which have carboxylic acid side chains, encompass free carboxylic acids, $C_{1-5}$alkyl and benzyl ester side chains. Alkyl is intended to include any straight or branched chain alkyl group of the indicated number of carbons.

The peptide mimics of this invention bind to HIV protease in a manner which mimics the binding of the natural substrate. The total number of peptide residues in B, Q, G, Y, and E is generally 3 to 5. The residues closest to the putative cleavage site of the peptide mimic are most important for binding. The residue corresponding to G may be a neutral, acidic or basic amino acid. Glu, Gln, Arg, Lys, Ser, Ala, β-Ala, Asn and Gly are suitable. Gln, Asn and Ala are especially preferred for G. The residue Q is preferably a hydrophilic residue, such as D- or L- Ser, Thr, Asp or His. Especially preferred are Thr and Ser.

B corresponds to an amino acid, which may be hydrophilic or hydrophobic, or it may be a covalent bond in the shorter peptides. The identity of B is not critical and a residue may be chosen for the favorable physicochemical and biochemical properties it confers on the overall peptide, such as water solubility and resistance to exopeptidases. The choice of a D-amino acid often confers resistance to exopeptidases when the D-amino acid is at the terminus of the peptide. When B is a covalent bond, it may be advantageous for Q to be a D-amino acid. When B is not a covalent bond, B is preferably a D- or L-amino acid chosen from Ala, β-Ala, Gly, Ile, Val, Leu, Met, His, Lys, Arg, Glx, Asx, Cys, Ser or Thr. For producing the smallest peptides of this invention which bind to retroviral protease, B is preferably a covalent bond.

Y and E may correspond to the same or different amino acids or a covalent bond. If Y and/or E are amino acids, they may be hydrophilic or hydrophobic. In much the same manner as B, the residues of Y and E may be used to confer favorable biochemical or physiochemical properties to the compound. Thereby, the use of hydrophilic residues may be used to confer desirably solubility properties or D-amino acids at the carboxy terminus may be used to confer resistance to exopeptidases. Preferably, at least one of Y and E is an amino acid selected from Ala, Gly, Ile, Leu, Met, Val, Arg, Lys, Thr, Ser, Cys, Glx or Asx. For the shorter chain compounds of this invention, Y or E may be absent, but being one or two amino acids is especially suitable. Ala, Gly, Ile, Met, Arg, Asx and Val are preferred. Valine is especially preferred.

The compounds of this invention may have asymmetric centers, for example, the 3-position ($R_1$) on the ring of Formula I, or in the 2-position (OH) on the ring in compounds such as those of Formula III hereabove, or in the side chain $(CHCR_4)C(=O)-(Y)_c-(E)_d-Z$, or in the side chain $A-B-(Q)_a-(G)_b-(NHCHR_3)-$. The synthesis described herein for preparing compounds of this invention may produce mixtures of diastereomers. The isomers may be separated by standard procedures such as by chromatography. All of the isomers of the compounds of Formula I, whether in racemic mixtures or as individual diastereomers, are included in Formula I and are within the scope of this invention.

When compounds of this invention are administered to an animal infected or potentially infected with HIV virus which is dependent upon a virally encoded protease for processing of viral polyproteins, HIV viral replication is inhibited and hence, disease progression is retarded.

The following compounds are included in, but in no way limit, the scope of this invention:

1) 2-[2-oxo-3-benzyl-5-(1-alanylamino-ethyl) -2,3,6,7-tetrahydro-1H-azepin-1-yl]-1-oxo-propyl-valinyl-valine methyl ester;
2) 2-[3-benzyl-5-(1-alanylamino-ethyl)-2,3,6,7-tetrahydro-1H-azepin-1-yl]-1-oxo-propyl-valinyl-valine methyl ester;
3) 2-[3-benzyl-5-(1-(phenylalanyl)amino-ethyl)-2,3,6,7-tetrahydro-1H-azepin-1-yl]-1-oxo-propyl-valinyl-valine methyl ester;
4) 2-[3-benzyl-5-(1-(alanyl-alanyl)amino-ethyl)-2,3,6,7-tetrahydro-1H-azepin-1-yl]-1-oxo-propyl -valinyl-valine methyl ester;
5) 2-[3-benzyl-5-(1-alanylamino-ethyl)-2,3,6,7-tetrahydro-1H-azepin-1-yl]-1-oxo-propyl-valine methyl ester;
6) 2-(2-hydroxy-3-benzyl-5-methyl-cyclohept-4-en-1-yl)-1-oxo-ethyl-valinyl valine methyl ester;
7) 2-(2-hydroxy-3-benzyl-5-methyl-cyclohept-5-en-1-yl)-1-oxo-ethyl-valinyl valine methyl ester;
8) 2-(2-hydroxy-3-benzyl-5-t-butyl-cyclohept -4-en-1-yl)-1-oxo-ethyl-valinyl valine methyl ester;
9) 2-(2-hydroxy-3-(4-imidazolyl)methyl-5-methyl-cyclohept-4-en-1-yl)-1-oxo-ethyl-valinyl valine methyl ester;
10) 2-(5-[(1S)-1-alanylamino-ethyl]-3-benzyl-2-hydroxy-cyclohept-4-en-1-yl)-1-oxo-ethyl-valinyl-valine methyl ester;

11) (2S) -t-butyl 2-(5,7-dioxo-6-benzyl-4-[(1R)-1-(benzyloxycarbonylalanyl)amino-ethyl]-2,3,4,5,6,7-hexahydro-1H,4H-1,4-diazepin-1-yl) -propanoate; p0 12) (2R)-2-(1-[(1R)-1-(N-t-butyloxycarbonylalanyl) amino-ethyl]-3-benzyl-4-hydroxy-2,3,4,5,6,7-hexahydro-1H-azepin-5-yl)-1-oxo-propyl-valinyl-valine methyl ester; and
13) (2S)-2-(2,3,4,5,6,7-hexahydro-1H,4H-3-benzyl-4-[(1R)-1-(benzyloxycarbonyl-alanylamino)-ethyl]-5-oxo-6-benzyl-1,4-diazepin-1-yl)-3-phenyl-1-oxo-propyl-valinyl-valine methyl ester.

The azepine compounds of Formula I, where V is N, are prepared by cyclizing a 6-substituted aminohex-3-enoic ester, then treating with appropriate reactants to add substituents as desired on the ring and to add amino acid residues on the amino and carbonyl groups in the substituents on V and W of the ring. Schemes 1 and 2 are directed to procedures for preparing azepin-2-one and tetrahydroazepine compounds of this invention, in particular, the compounds of Examples 1 and 2.

Schemes 3 and 4 outline procedures for compounds of Formula I where $R_2$ is hydroxy and V and W are C.

Scheme 5 relates to a procedure for preparing diamide compounds of Formula I where V and W are N, and R and $R_2$ are =O.

In Scheme 6, a procedure for compounds of Formula I where V is C, W is N, R is =O and $R_2$ is OH is outlined.

Scheme 7 relates to a procedure for compounds of Formula I where V and W are N, R is =O and $R_2$ is 2H.

Other compounds of the invention are prepared by cyclization or ring expansion to prepare the seven-membered ring and then adding substituents and, particularly, optionally adding amino acid residues in the 1- and 5-positions on the ring as outlined in Scheme 8. These processes are also an object of this invention.

Scheme 1

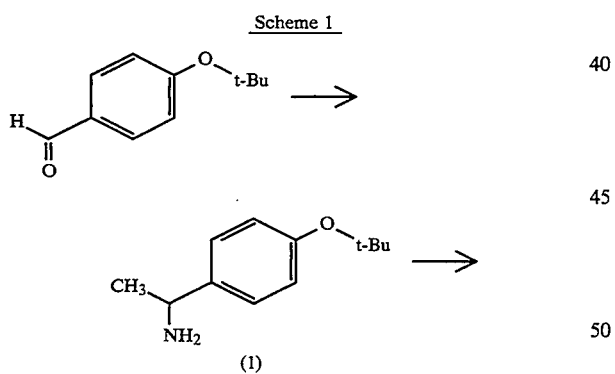

(1)

(2)

(3)

-continued
Scheme 1

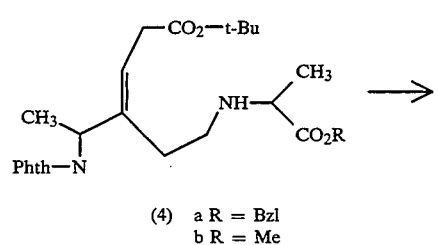

(4)  a R = Bzl
     b R = Me

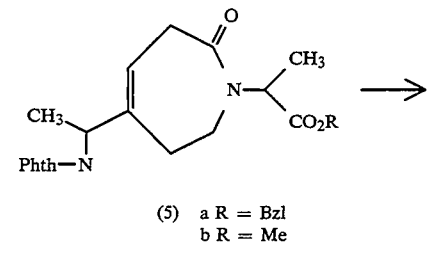

(5)  a R = Bzl
     b R = Me

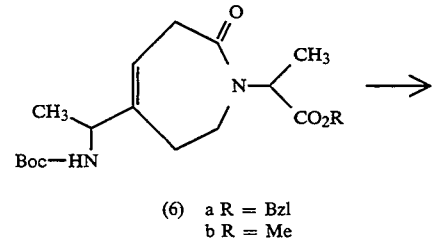

(6)  a R = Bzl
     b R = Me

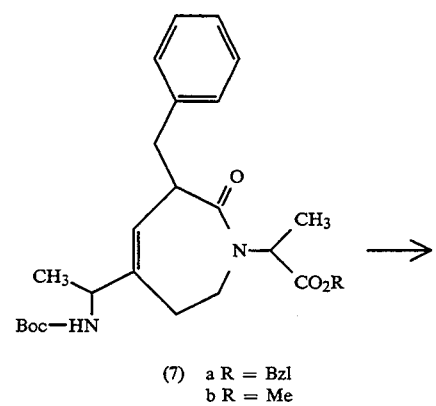

(7)  a R = Bzl
     b R = Me

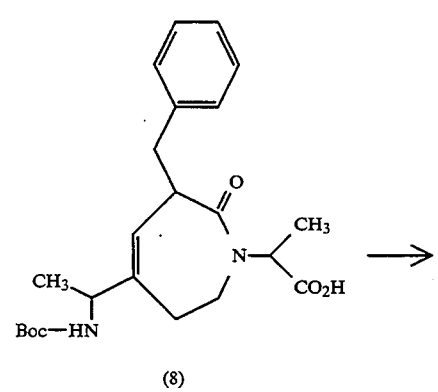

(8)

-continued
Scheme 1
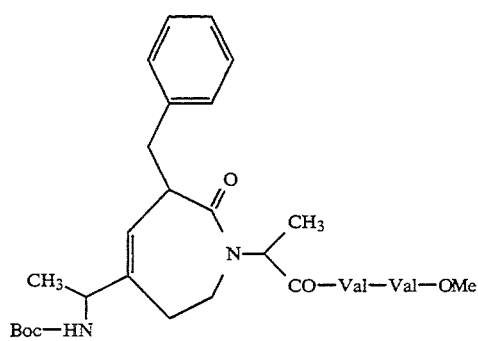
(9)
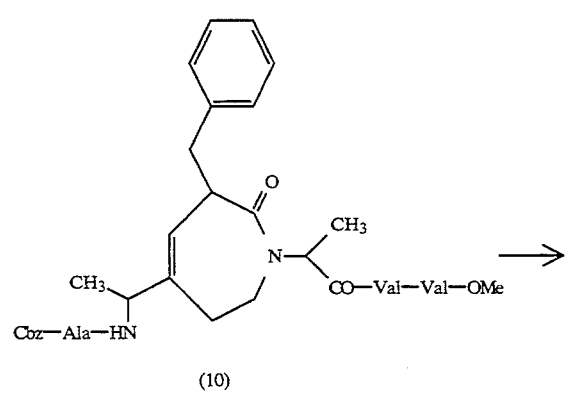
(10)
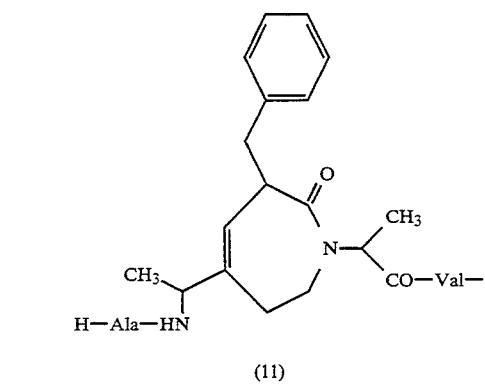
(11)
Scheme 2
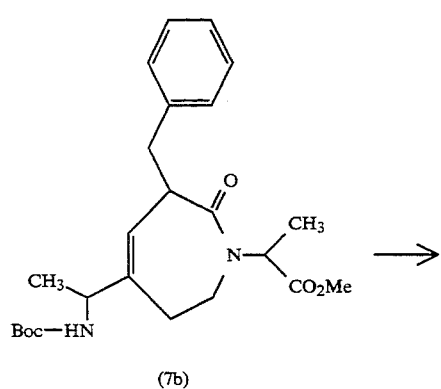
(7b)
-continued
Scheme 2
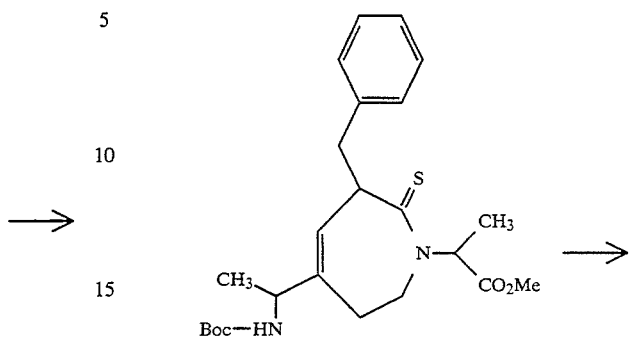
(12)
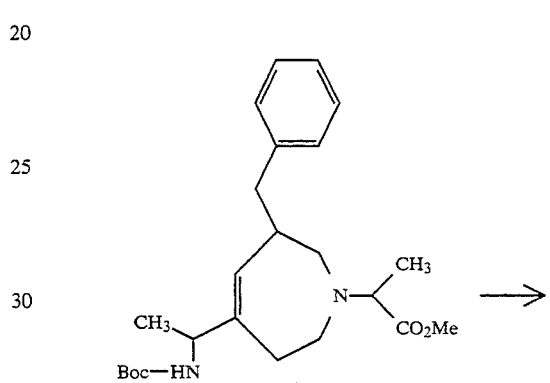
(13)
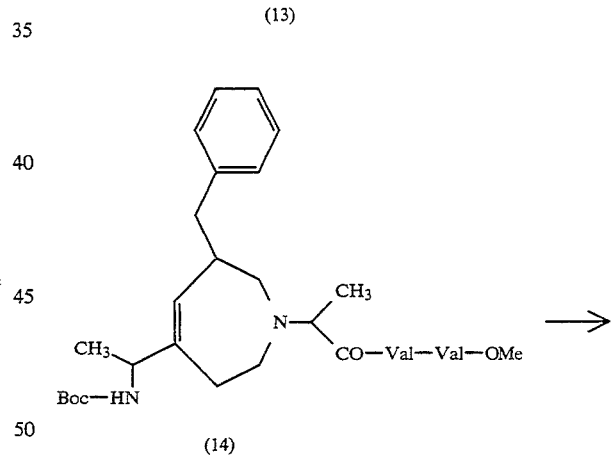
(14)
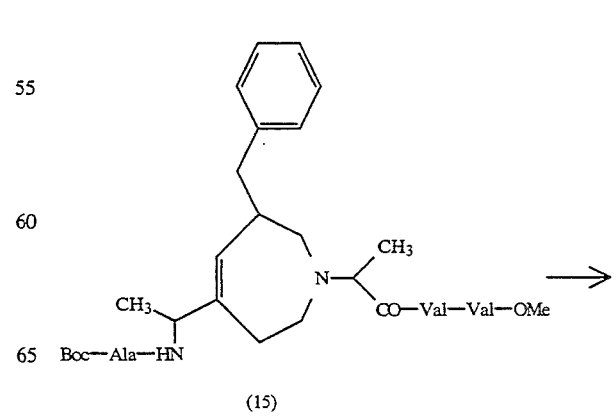
(15)

-continued
Scheme 2
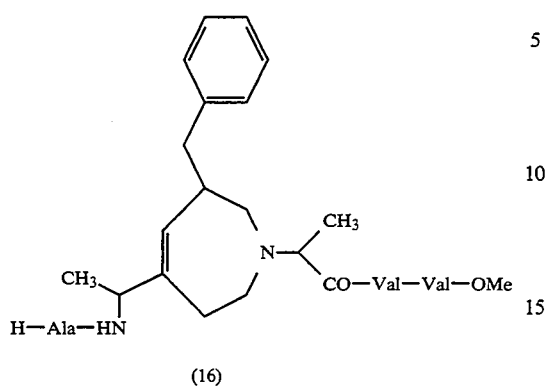
(16)
Scheme 3
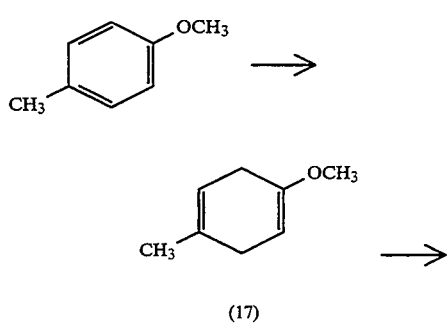
(17)
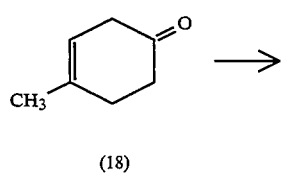
(18)
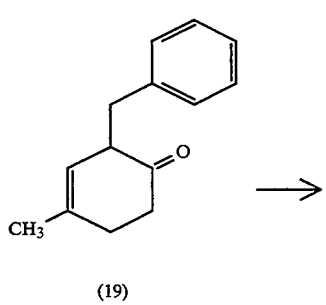
(19)
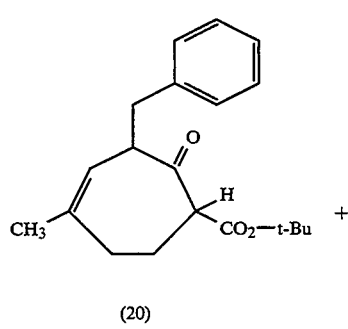
(20)
+
-continued
Scheme 3
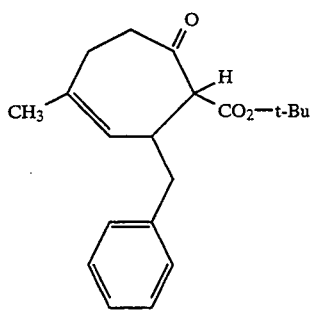
(21)
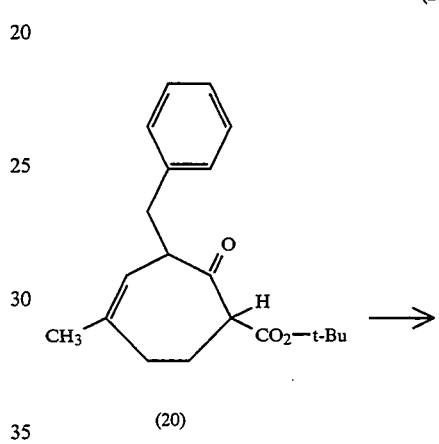
(20)
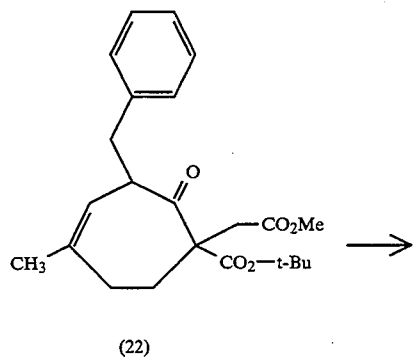
(22)
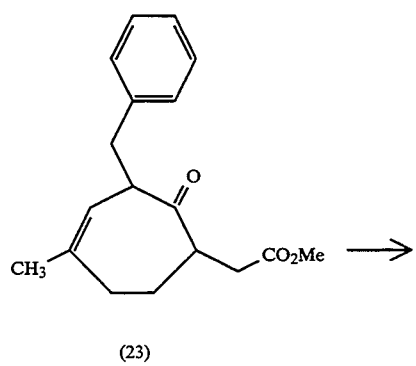
(23)

-continued
Scheme 3
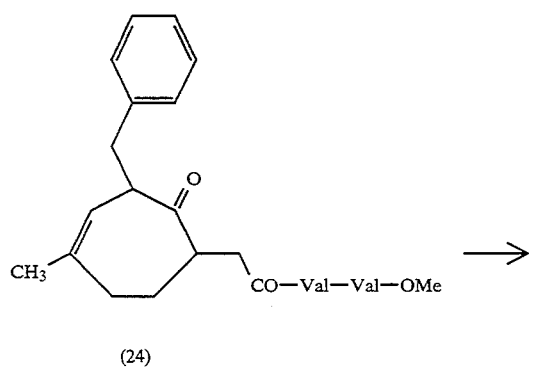
(24)
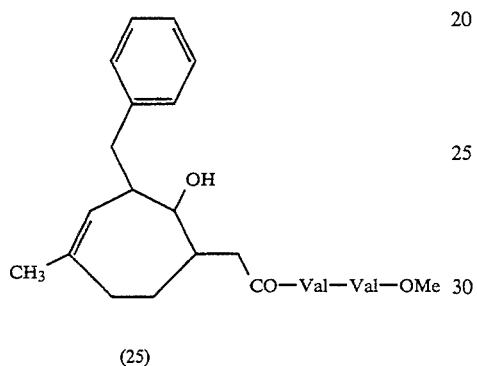
(25)
Scheme 4
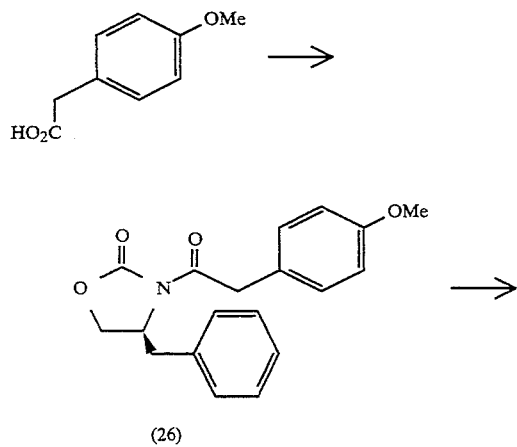
(26)
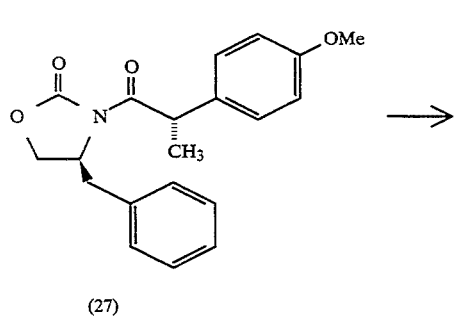
(27)
-continued
Scheme 4
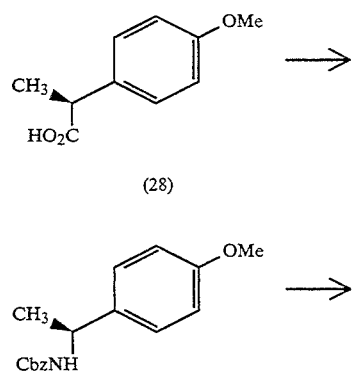
(28)
(29)
(30)
(31)
(32)
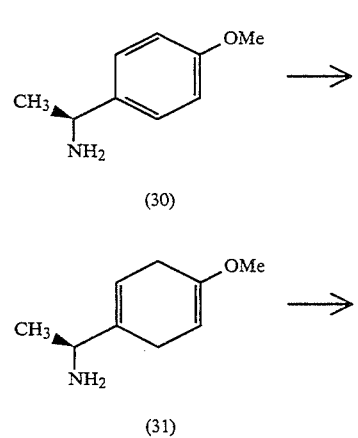
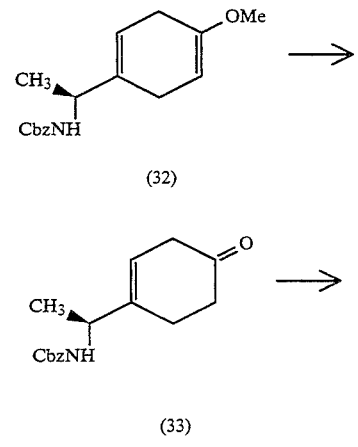
(33)
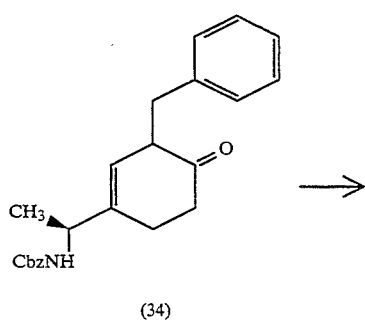
(34)

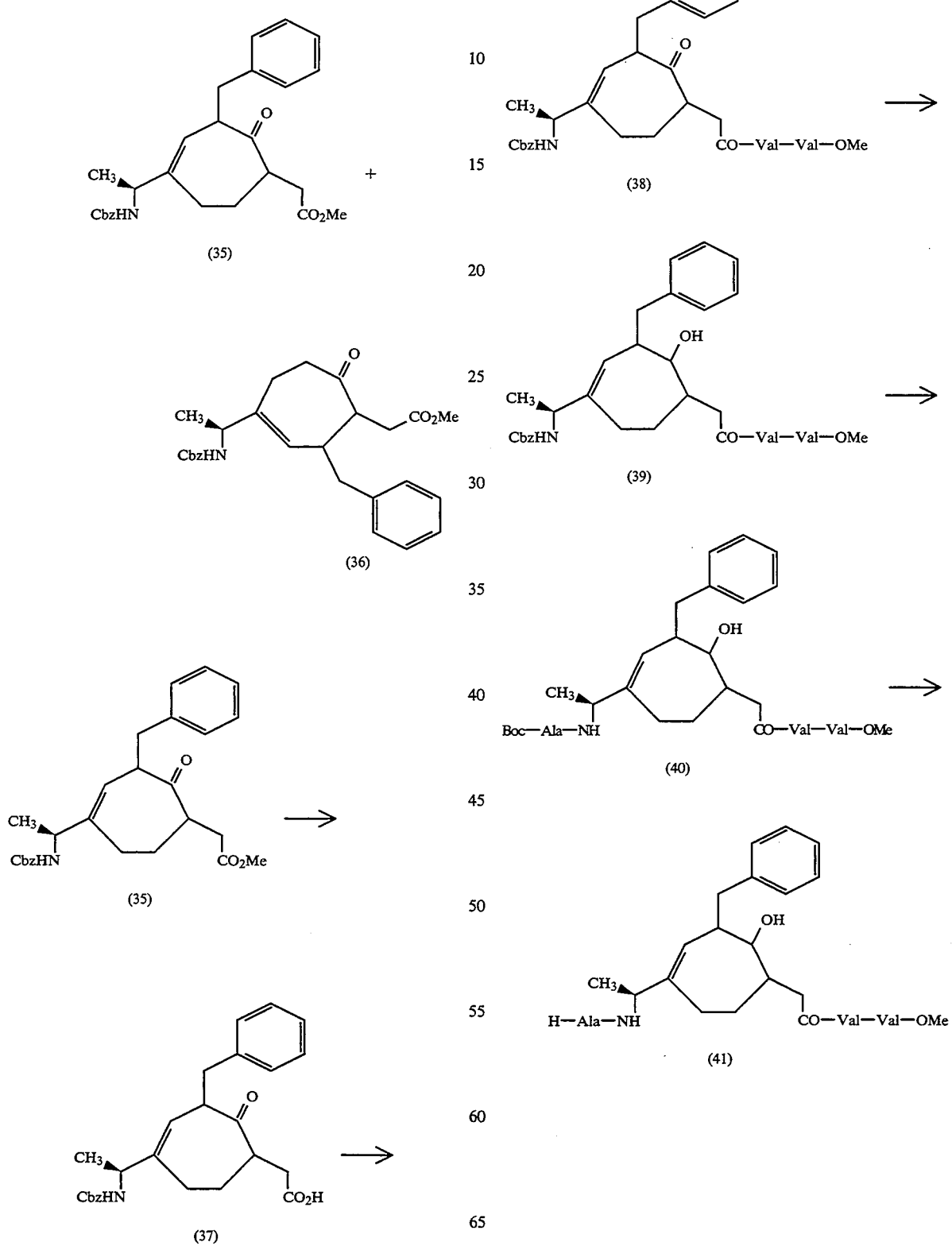

Scheme 5
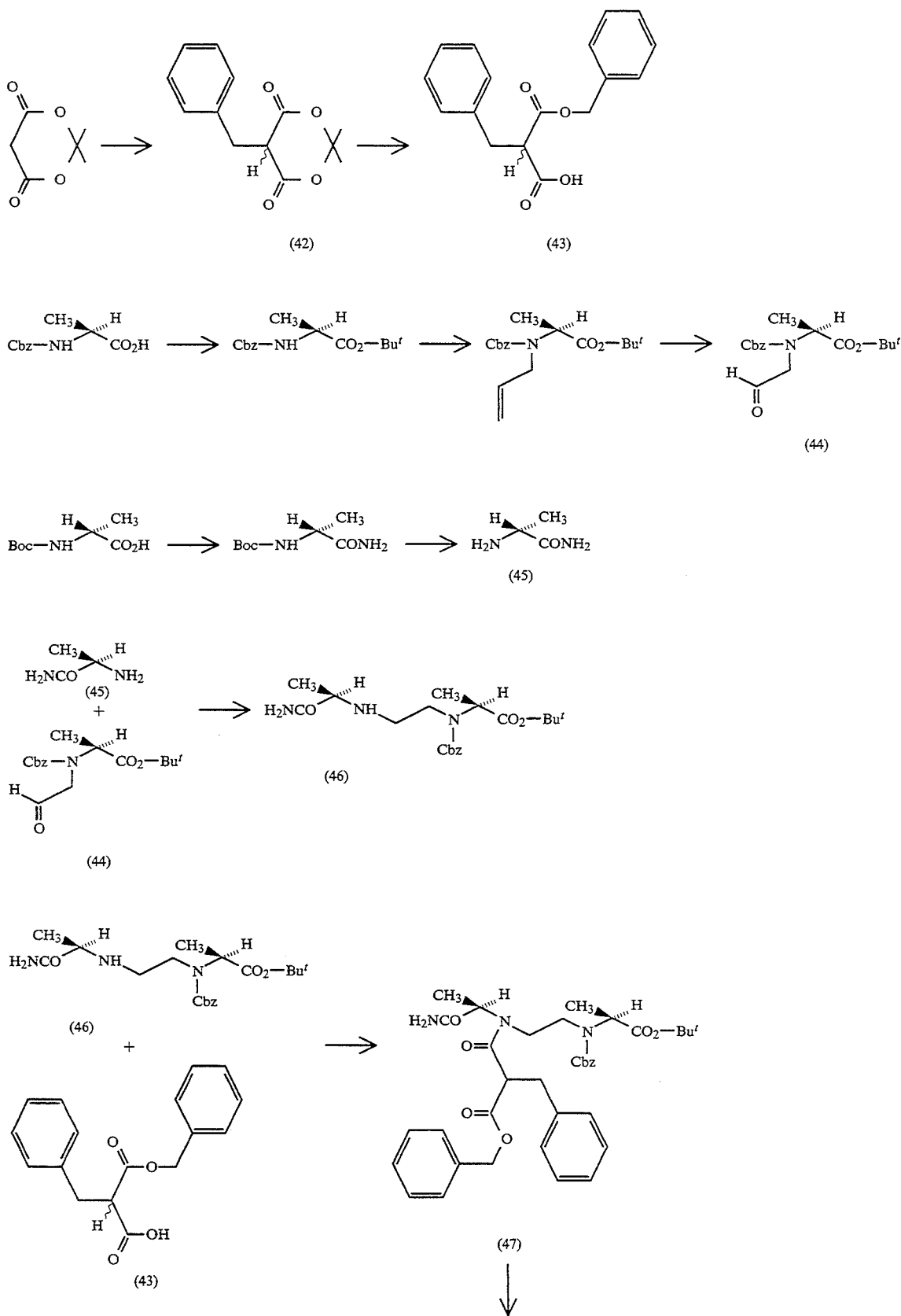

-continued
Scheme 5
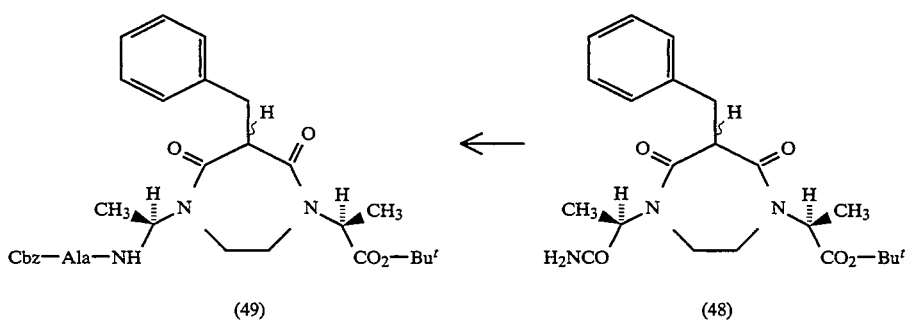
Scheme 6
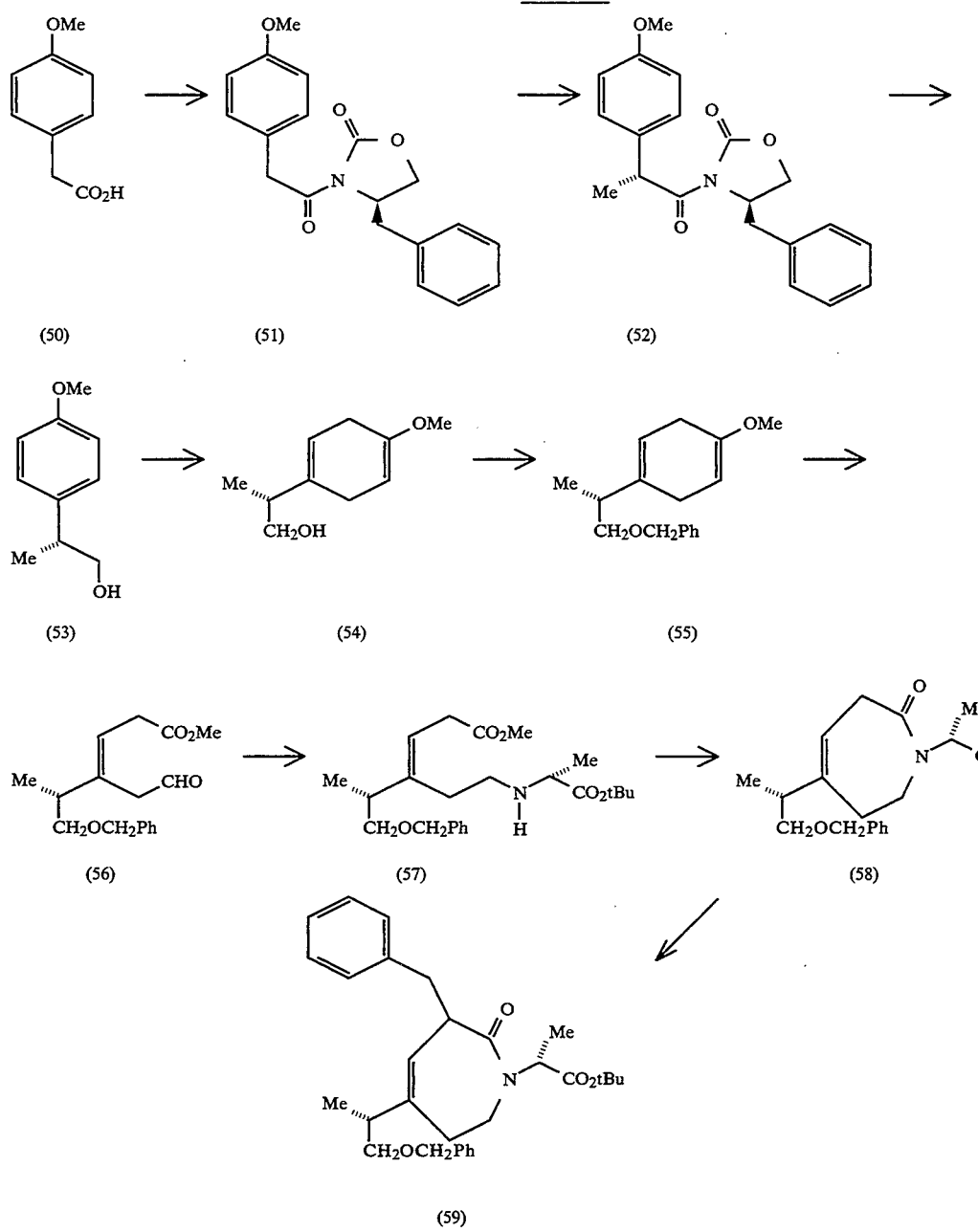

-continued
Scheme 6
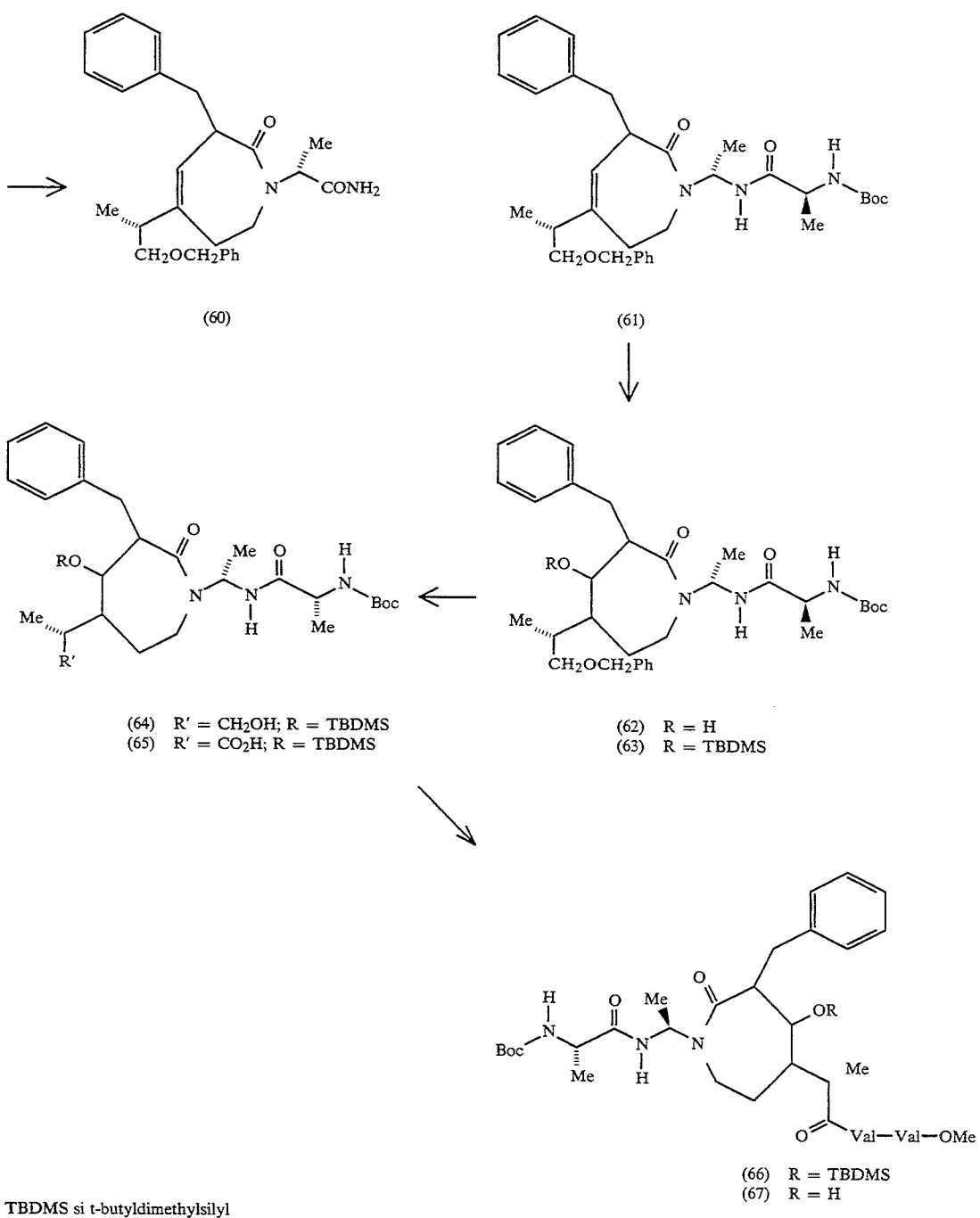
TBDMS si t-butyldimethylsilyl
Scheme 7
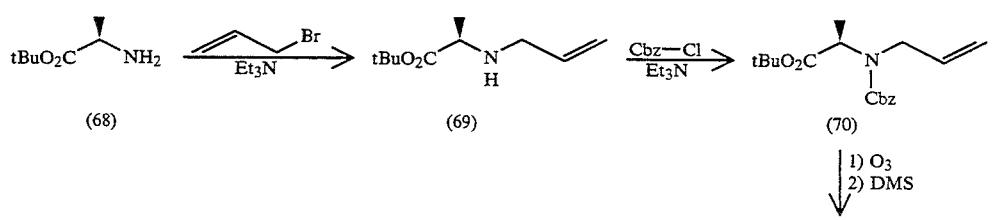
1) O₃
2) DMS -continued
Scheme 7
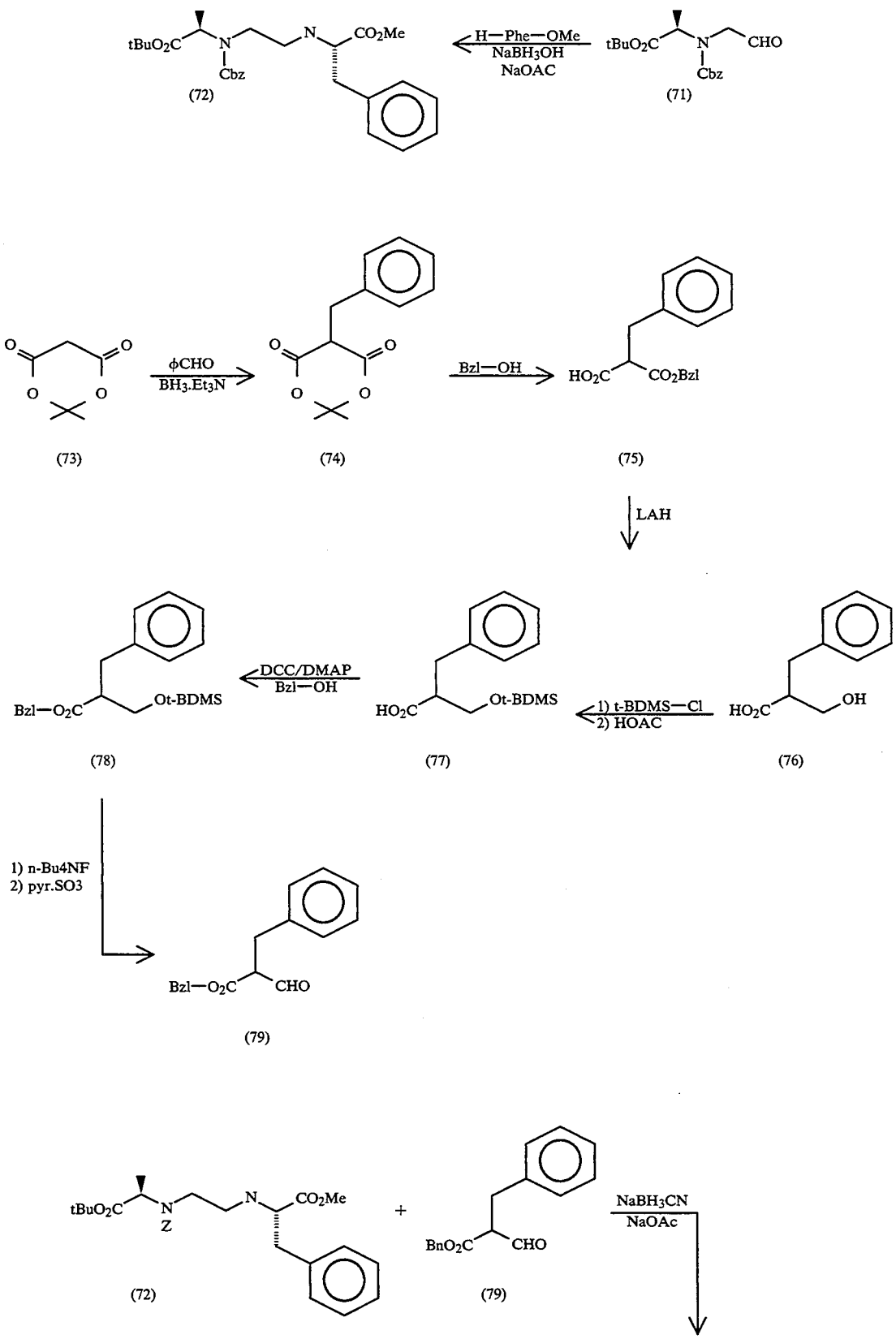

-continued
Scheme 7
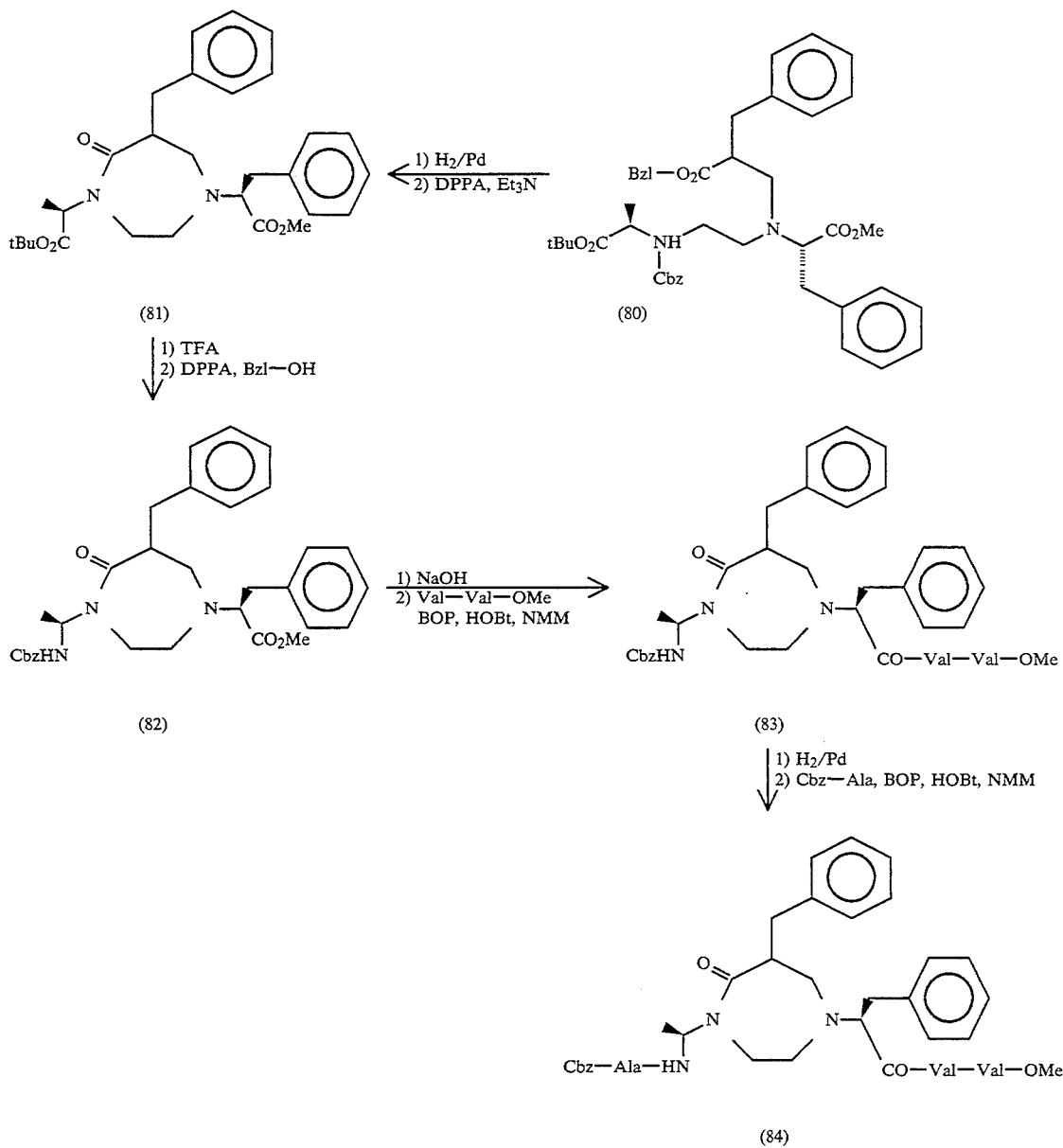
Scheme 8
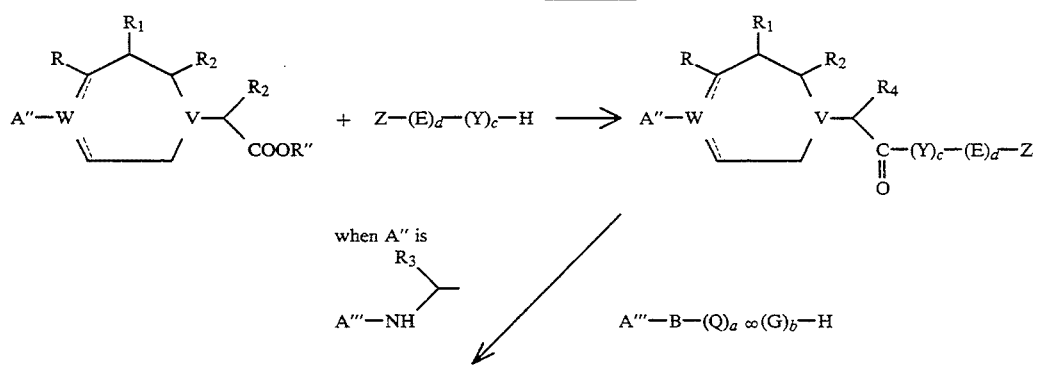

-continued
Scheme 8

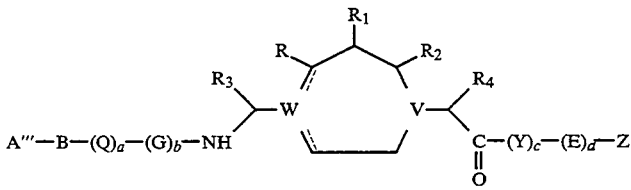

in which:

A" is A' or

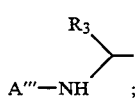

R" is hydrogen or lower alkyl;
A''' is H or an amino protecting group; and the other terms are as in Formula I; and optionally removing the protecting group A'''; or converting a compound of the formula:

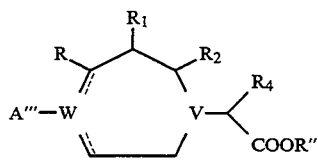

to the following compound of the formula:

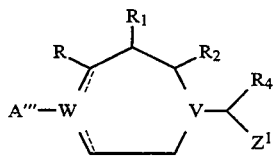

in which Z' is Z with any necessary protecting groups, and when A" is

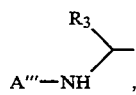

reacting with A"—B—(Q)$_a$—(G)$_b$—H to give a compound of the formula:

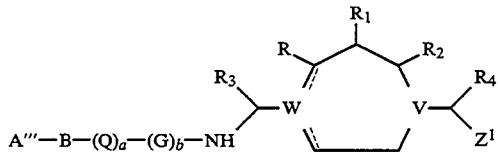

and optionally removing protecting group A" and any protecting groups in Z'.

The protease inhibiting properties of the compounds of this invention are demonstrated by the ability to inhibit the hydrolysis of a peptide substrate by rHIV protease. The data in the following table is representative of inhibition produced by these compounds.

TABLE I

| Compounds of Example No | Inhibition of rHIV Protease |
|---|---|
| 1 | 100 μM |
| 2 | 0.6 μM |
| 3 | 3.6 μM |

Pharmaceutical compositions of the compounds of this invention, or derivatives thereof, may be formulated as solutions or lyophilized powders for parenteral administration. Powders may be reconstituted by addition of a suitable diluent or other pharmaceutically acceptable carrier prior to use. The liquid formulation is generally a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride or sodium citrate.

A preferred composition for parenteral administration may additionally be comprised of a quantity of the compound encapsulated in a liposomal carrier. The liposome may be formed by dispersion of the compounds in an aqueous phase with phospholipids, with or without cholesterol, using a variety of techniques, including conventional handshaking, high pressure extrusion, reverse phase evaporation and microfluidization. Such a carrier may be optionally directed toward its site of action by an immunoglobulin or protein reactive with the viral particle or infected cells. An example of such a protein is the CD-4 T-cell glycoprotein, or a derivative thereof, such as sCD-4 (soluble CD-4), which is reactive with the glycoprotein coat protein of the human immunodeficiency virus (HIV).

Alternately, these compounds may be encapsulated, tableted or prepared in a emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline and water. Solid carriers include starch, lactose, calcium sulfate dihydrate, terra alba, magnesium stearate or stearic acid, talc, pectin, acacia, agar or gelatin. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms.

When a liquid carrier is used, the preparation will be in the form of a syrup, elixir, emulsion or an aqueous or non-aqueous suspension. Such a liquid formulation may be administered directly p.o. or filled into a soft gelatin capsule.

For rectal administration, a pulverized powder of the compounds of this invention may be combined with excipients such as cocoa butter, glycerin, gelatin or polyethylene glycols and molded into a suppository. The pulverized powders may also be compounded with an oily preparation, gel, cream or emulsion, buffered or unbuffered, and administered through a transdermal patch.

Suitably, a pharmaceutical composition comprises a compound of this invention, azidothymidine and a pharmaceutically acceptable carrier.

The compounds of Formula I are used to induce anti-HIV activity in patients who are infected with the virus and require such treatment. The method of treatment comprises the administration orally, parenterally, buccally, transdermally, rectally or by insufflation, of an effective quantity of the chosen compound, preferably dispersed in a pharmaceutical carrier. Dosage units of the active ingredient are selected from the range of 0.05 to 15 mg/kg. These dosage units may be administered one to ten times daily for acute or chronic infection.

The Examples which follow serve to illustrate this invention. The Examples are intended to in no way limit the scope of this invention, but are provided to show how to make and use the compounds of this invention.

In the Examples, all temperatures are in degrees Celsius. Amino acid analyses were performed upon a Dionex Autoion 100. Analysis for peptide content is based upon Amino Acid Analysis. FAB mass spectra were performed upon a VG Zab mass spectrometer using fast atom bombardment. NMR were recorded at 250 MHz using a Bruker AM250 spectrometer or at 90 MHZ using a Varian EM 390 spectrometer. Multiplicities indicated are: s=singlet, d=doublet, t=triplet, q=quartet, m=multipier and br indicates a broad signal. All spectra use tetramethylsilane as an internal standard.

INHIBITION OF HIV PROTEASE ACTIVITY

A typical assay contains 10 mL MENDT buffer (50 mM Mes (pH 6.0; 2-(N-morpholino)ethanesulfonic acid), 1 mM EDTA, 1 mM dithiothreitol, 200 mM NaCl, 0.1% Triton X100); 2, 3, or 6 mM N-acenyl-L-arginyl-L-alanyl-L-seryl-L-glutaminyl-L-asparaginyl-L-tyrosyl-L-prolyl-L-valyl-L-valinamide (Ac-Arg-Ala-Ser-Gln-Asn-Tyr-Pro-Val-Val-Val-NH$_2$; K$_m$=7 mM); and micromolar and sub-micromolar concentrations of synthetic compounds. Following incubation at 37° C. for several min, the reaction is initiated with purified 0.01–1 mg HIV protease. Reaction mixtures (37° C.) are quenched after 10–20 min with an equal volume of cold 0.6N trichloroacetic acid, and, following centrifugation to remove precipitated material, peptidolysis products are analyzed by reverse phase HPLC (Beckman Ultrasphere ODS, 4.5 mm×25 mm; mobile phase; 5–20% acetonitrile/H$_2$O—0.1% TFA (15 min), 20% acetonitrile/H$_2$O—0.1% TFA (5 min) at 1.5 mL/min, detection at 220 nm. The elution positions of Ac-Arg-Ala-Ser-Gln-Asn-Tyr-Pro-Val-Val-NH$_2$ (17–18 min) and Ac-Arg-Ala-Ser-Gln-Asn-Tyr (10–11 min) are confirmed with authentic material. Initial rates of Ac-Arg-Ala-Ser-Gln-Asn-Tyr formation are determined from integration of these peaks, and typically, the inhibitory properties of the synthetic compounds are determined from slope/intercept analysis of a plot of 1/v vs. [inhibitor] (Dixon analysis). K$_i$ values resulting from this type of primary analysis are accurate for competitive inhibitors only, and under conditions in which the Michaelis constant of the substrate used is well determined.

EXAMPLE 1

Preparation of 2-[3-benzyl-5-(1-alanylamino-ethyl)-2,3,6,7-tetrahydro-1H-2-oxo-azepin-1-yl]-1-oxo-propyl-valinyl-valine methyl ester Compound 11 of Scheme 1 diagrammed hereabove is prepared as follows:

a.) 1-(4-t-butyloxy-phenyl)-ethylamine (1)

To a stirred solution of p-t-butyloxybenzaldehyde (45 g, 250 mmol) in dry THF (100 mL) under Ar at 0° C. was added a solution of lithium hexamethyldisilazane (280 mL, 1N in THF). The reaction was allowed to warm to room temperature and stirred for 15 min. A solution of methylmagnesium bromide (170 mL, 3N in ether) was next added and the reaction heated at reflux, under argon, for 2 days. The reaction was slowly poured into cold saturated ammonium chloride (500 mL) with swirling, extracted with ether (2×300 mL), washed with brine, dried over sodium sulfate and evaporated to dryness. Short path distillation under high vacuum (bp 100° C., 0.005 mm Hg) afforded product as a clear liquid (32.3 g, 71%): GC RT 6.88 min. (HP 530 mµ×20 m methylsilicone column, He carrier flow rate 20 mL/min., 100° C. init. temp., 3 min. init. time, 10° C./min. rate, 180° C. final temp., 1 min. final time); $^1$H NMR (CDCl$_3$) δ1.3 (3H, d, J=6 Hz), 1.45 (2H, s), 4.05 (1H, q), 7.1 (4H, q).

b.) 1-t-butyloxy-4-(1-amino-ethyl)-1,4-cyclohexadiene (2)

To a stirred solution of the above amine (1) (32.3 g) and t-butanol (14.5 g) in dry THF (200 mL) at −78° C. was condensed NH$_3$ (1000 mL) via a cold finger. Lithium wire (3.3 g) was then added in portions with vigorous stirring. The now blue reaction mixture was stirred for 1 h at −78° C. then slowly quenched with ethanol until the reaction turned white. The reaction was allowed to go to room temperature and warmed to allow the NH$_3$ to evaporate. The slurry was taken up in ether, washed with water, dried over sodium sulfate and evaporated to give the product as a clear liquid. (32.6 g, >95% pure): GC RT 7.26 min. (HP 530 mµ×20 m methylsilicone column, He carrier flow rate 20 mL/min., 100° C. init. temp., 3 min. init. time, 10° C./min. rate, 180° C. final temp., 1 min. final time); $^1$H-NMR (CDCl$_3$) δ1.1 (3H, d, J=6 Hz), 1.3 (9H, s), 1.4 (2H, s), 3.45 (1H, q), 5.1 (1H, s), 5.6 (1H, s).

c.) t-butyl 4-(1-phthalylamino-ethyl)-6-oxo-(Z)-hex-3-enoate (3)

To a stirred solution of the above diene (2) (32.6 g) in THF (300 mL) was added N-ethoxycarbonylphthalimide (36.6 g). After 2 h NEt$_3$ (24 mL) was added and the reaction stirred overnight at room temperature. TLC indicated the reaction was complete. TLC R$_f$0.71 (silica gel, 30% EtOAc, n-hexane) The reaction was evaporated to dryness and re-evaporated several times with toluene to remove any excess NEt$_3$. The crude phthalated diene was taken up in (3:1) methanol, CH$_2$Cl$_2$ (500 mL) and with stirring at −78° C., O$_3$ was passed through the reaction until most of the diene had disappeared by TLC. The reaction was then flushed with Ar to remove excess $O_3$ and dimethylsulfide (30 mL) added. The reaction was allowed to warm to room temperature and stirred for 3 h. After evaporating the solvent, the product (3) was obtained as an oil by flash chromatography on silica gel eluted with 20% ethylacetate in n-hexane (23.4 g, 39%): TLC $R_f$ 0.49 (silica, 30% EtOAc, n-hexane); $^1$H NMR (CDCl$^3$) δ1.5 (9H, s), 1.7 (3H, d, J=7 Hz), 3.05 (2H, d, J=7 Hz), 3.3 (2H, s), 5.05 (1H, q), 6.2 (1H, t), 7.85 (4H, m), 9.65 (1H, t).

d.) N-[5-t-butyloxycarbonyl-3-(1-phthalylamino-ethyl)-(Z)-pent-3-enyl]-alanine benzyl ester (4a)

To a stirred solution of the above aldehyde (3) (12.5 g) in methanol (200 mL) under Ar was added L-alanine benzyl ester p-toluenesulfonic acid salt (25 g), NEt$_3$ (4.9 mL) and NaBH$_3$CN (4.4 g) in portions over 5 min. The reaction was stirred for 16 h, evaporated to dryness, taken up in ethyl acetate, washed with water, dried over Na$_2$SO$_4$ and re-evaporated. Product, as a mixture of diastereomers, was obtained by flash chromatography on silica gel eluted with 30–40% EtOAc in n-hexane. (3.77 g, 21%): TLC $R_f$ 0.24 (silica, 40% EtOAc, n-hexane); $^1$H NMR (CDCl$_3$) δ1.2 (3H, d, J=6 Hz), 1.45 (9H, s), 1.65 (3H, d, J=7 Hz), 1.7–2.2 (5H, m), 3.1 (2H, d, J=6 Hz), 3.35 (1H, q), 4.9 (1H, q), 5.15 (2H, s), 5.9 (1H, m), 7.4 (5H, s), 7.8 (4H, m).

e.) 1-(1-benzyloxycarbonyl-ethyl)-5-(1-phthalylamino-ethyl)-2,3,6,7-tetrahydro-1H-azepin-2-one (5a)

To the above diester (4a) (3.77 g) was added 80% TFA in CH$_2$Cl$_2$ (75 mL). After stirring for 1 h at room temperature, the reaction was evaporated to dryness and re-evaporated from toluene several times to remove any trace amounts of TFA. To a stirred solution of the above in DMF (300 mL) at 0° C. under Ar was added NEt$_3$ (2 mL), NaHCO$_3$ (3 g) and diphenylphosphoryl azide (3.12 mL). The reaction was stirred under Ar at 0° C. for 2 days. After stripping off the solvent, the residue was taken up in ethyl acetate, washed with water, dried over MgSO$_4$, evaporated and purified by flash chromatography on silica gel eluted with 45–50% EtOAc in n-hexane affording product, a mixture of diastereomers, as an oil. (1.95 g, 60%): TLC $R_f$ 0.32 (silica, 50% EtOAc, n-hexane); $^1$H NMR (CDCl$_3$) δ1.43 (3H, dd), 1.6 (3H, d, J=7 Hz), 2.25 (2H, br s), 3.2–3.8 (4H, m), 4.75 (1H, q), 5.15 (2H, s), 5.2 (1H, q), 5.85 (1H, t), 7.35 (5H, s), 7.75 (4H, m).

f.) 1-(1-benzyloxycarbonyl-ethyl)-5-(1-t-butyloxycarbonyl-amino-ethyl)-2,3,6,7-tetrahydro-1H-azepin-2-one (6a)

To a stirred solution of the above (5a) (1.95 g) in ethanol (60 mL) was added hydrazine monohydrate (0.5 mL). The reaction was stirred for 3 days at room temperature. The resulting white suspension was stripped of solvent, triturated with chloroform (100 mL) and filtered to remove any insoluble material. After rinsing with fresh chloroform (10 mL) the filtrate was evaporated to dryness. The oil which remained was taken up in THF (75 mL) and di-t-butyl-dicarbonate (1.9 g) was added with stirring. The reaction was stirred for 16 h at room temperature and evaporated to dryness. The product, a mixture of diastereomers, was purified by flash chromatography on silica gel eluted with 40–50% EtOAc in n-hexane. (1.14 g, 62%): TLC $R_f$ 0.25 (silica, 40% EtOAc, n-hexane); $^1$H NMR (CDCl$_3$) δ1.15 (3H, d, J=6 Hz), 1.45 (9H, s), 1.5 (3H, d, J=6 Hz), 2.3 (2H, br s), 3.2–4.5 (4H, m), 4.05 (1H, q), 4.7 (1H, d, J=9 Hz), 5.2 (2H, s), 5.6 (1H, t), 7.4 (5H, s).

g.) 1-(1-benzyloxycarbonyl-ethyl)-3-benzyl-5-(1-t-butyloxy-carbonylamino-ethyl)-2,3,6,7-tetrahydro-1H-azepin-2-one-(7a)

To a stirred solution of lithium diisopropylamine made from diisopropylamine (1 mL) in THF (100 mL) and butyl lithium (2.6 mL, 2.5N butyl lithium in hexane) was added at −78° C. under Ar the above Boc-benzylester (6a) (1.1 g) dissolved in THF (20 mL). After stirring for 15 min at − 78° C., benzylbromide (0.63 mL) was added in one portion. The reaction was stirred for 30 min and quenched with sat. NH$_4$Cl. After warming to room temperature the reaction was extracted with EtOAc washed with brine, dried over MgSO$_4$ and evaporated. The product, as a mixture of diastereomers, was obtained by flash chromatography on silica gel eluted with 20–50% EtOAc in n-hexane. (0.23 g) Unreacted starting material was also recovered (0.78 g) which was realkylated as before to give a total of 0.5 g product. TLC $R_f$ 0.60 (silica, 40% EtOAc, n-hexane); $^1$H NMR (CDCl$_3$) δ1.05 (3H, dd), 1.4 (9H, s), 1.5 (3H, d), 2.0–3.5 (6H, m), 3.5–4.1 (2H, m), 4.4 (1H, m), 5.2 (2H, s), 5.35 (1H, br s), 7.25 (5H, s), 7.4 (5H, s), MS DCI, NH$_3$ (M+H)+ =417.5.

h.) 1-(1-carboxy-ethyl)-3-benzyl-5-(1-t-butyloxycarbonylamino-ethyl)-2,3,6,7-tetrahydro-1H-azepin-2-one (8)

To a stirred solution of the above benzyl ester (7a, 0.5 g) in dioxane (10 mL) was added aqueous 1N NaOH (2 mL). After stirring for 16 h, aq 1N HCl (2 mL) was added and the solution extracted with EtOAc (100 mL), washed with brine, dried over MgSO$_4$ and evaporated to dryness. Pure acid, as a mixture of isomers, was obtained by flash chromatography on silica gel eluted with (97:3:0.1) CHCl$_3$, MeOH, HOAc. (0.48 g): TLC $R_f$ 0.4 (silica, 95:4:1, CHCl$_3$:MeOH:HOAc); $^1$H NMR (CDCl$_3$) δ1.1 (3H, d, J=6 Hz), 1.4 (9H, s), 1.45 (3H, d, J=6 Hz), 2.0–3.0 (4H, m), 3.2–3.7 (2H, m), 3.7–4.3 (3H, m), 5.2 (1H, m), 5.35 (1H, br s), 7.3 (5H, s), 9.6 (1H, br s).

i.) 2-[2-oxo-3-benzyl-5-(1-t-butyloxycarbonylamino-ethyl)-2,3,6,7-tetrahydro-1H-azepin-1-yl]-1-oxo-propyl-valinyl-valine methyl ester (9)

To a stirred solution of the above acid (8) in DMF (15 mL) was added HCl.Val-Val-OMe (0.4 g), HOBt (0.27 g), NEt$_3$ (0.8 mL) and BOP reagent (0.62 g). The reaction was stirred for 16 h at room temperature and evaporated to dryness. The product, as a mixture of diastereomers,was obtained as a solid foam by flash chromatography on silica gel eluted with 65% EtOAc in n-hexane. (0.64 g, 83%): TLC $R_f$ 0.64 (silica, 70% EtOAc, n-hexane); $^1$H NMR (CDCl$_3$) δ0.8–1.0 (12H, dd) valine g (CH$_3$)2's, 1.15 (3H, d, J=6 Hz) alanine βCH$_3$'s, 1.4 (9H, s) Boc t-butyl, 3.7 (3H, s) methyl ester, 5.4 (1H, br s) olefinic CH, 7.3 (5H, s) phenyl.

j.) 2-[2-oxo-3-benzyl-5-(1-(N-benzyloxycarbonyl)alanylamino-ethyl-2,3,6,7-tetrahydro-1H-azepin-1-yl]-1-oxo-propyl-valinyl-valine methyl ester (10)

The above product (9, 0.64 g) was treated with saturated HCl/dioxane (50 mL) with stirring for 1 h at room temperature. The reaction was evaporated, triturated with ether and filtered. The dried white powder was dissolved in DMF (15 mL) to which was added with stirring Cbz-Ala (0.29 g), HOBt (0.25 g), NEt$_3$ (0.13 mL), followed by DCC (0.29 g). The reaction was stirred for 16 h at room temperature and evaporated to dryness. The product, as a mixture of diastereomers, was obtained by silica gel chromatography eluted with 1% MeOH in CHCl$_3$ (0.13 g): TLC $R_f$ 0.38 (silica, 5%

MeOH, CHCl₃); ¹H NMR (CDCl₃) δ0.8–1.0 (12H, m) valine γ(CH₃)₂'s, 1.2 (3H, d, J=6 Hz), 1.35 (3H, d, J=6 Hz), 1.4 (3H, d, J=6 Hz) alanine βCH₃'s, 3.75 (3H, s) methyl ester, 5.1 (2H, s) urethane CH₂, 7.3 (5H, s) ring phenyl, 7.4 (5H, s) urethane phenyl; MS (FAB, DTT/DTE) (M+H)⁺=734.6, (M−H)⁻=732.6.

k.) 2-[2-oxo-3-benzyl-5-(1-alanylamino-ethyl)-2,3,6,7-tetrahydro-1H-azepin-1-yl]-1-oxo-propyl-valinyl-valine methyl ester (11)

100 mg of (10) was treated with HF (20 mL) at 0° C. for 30 min in an HF apparatus and evaporated to dryness by a water aspirator. The residue was dried under high vacuum then triturated and filtered from ether. The solid was dissolved in 10% HOAc in water and lyophilized to yield the title compound as a white fluffy solid. Reverse phase HPLC (Apex C-18, 40% CH₃CN, 0.1% TFA, 60% 0.1% TFA, H₂O) indicated 3 peaks in a ratio of (1:1:2). Each peak was isolated by preparative HPLC and shown by MS (FAB, DTT/DTE) to have identical mass (M+H)⁺=600, (M−H)⁻=598.

EXAMPLE 2

Preparation of 2-[3-benzyl-5-(1-alanylamino-ethyl)-2,3,6,7-tetrahydro-1H-azepin-1-yl]-1-oxo-propyl-valinyl-valine methyl ester (16)

Compound 16 of Scheme 2 diagramed hereabove is prepared as follows:

a.) N-[5-t-butyloxycarbonyl-3-(1-phthalylamino-ethyl)-(Z)-pent-3-enyl]-alanine methyl ester (4b)

To a stirred solution of HCl-alanine methyl ester (13 g) in methanol (250 mL) at room temperature under Ar was added sodium acetate (9.8 g) followed by N-phthalylester aldehyde (3) (21.3 g) prepared as in Example 1. After stirring for 5 min the reaction was cooled in an ice bath and NaBH₃CN (5.7 g) was added in portions over 15 min (foaming). The reaction was stirred for 16 h at room temperature, evaporated to dryness, taken up in EtOAc, washed with H₂O, dried over Na₂SO₄ and evaporated. Flash chromatography on silica gel eluted with 40% EtOAc in n-hexane afforded the product, a mixture of diastereomers, as an oil (13.8 g, 52%): TLC R_f 0.36 (silica, 50% EtOAc, n-hexane).

b.) 1-(1-methoxycarbonyl-ethyl)-5-(1-phthalylamino-ethyl)-2,3,6,7-tetrahydro-1H-azepin-2-one (5b)

To a stirred solution of the above t-butyl ester (4b) (13.8 g) was added 80% TFA in CH₂Cl₂ (100 mL). After 1 h at room temperature the reaction was evaporated to dryness. The residue was twice taken up in sat. HCl dioxane and re-evaporated to dryness. The residue was next dissolved in DMF (500 mL) and with stirring under Ar at 0° C. was added NEt₃ (6.6 mL), NaHCO₃ (9.8 g), and finally diphenylphosphoryl azide (10.1 mL). The reaction was kept at 0° C. cooled in a dewar flask and stirred for 2 days. The reaction was evaporated to dryness, taken up in EtOAc, washed with H₂O, brine, dried over MgSO₄ and evaporated. Flash chromatography on silica gel eluted with 50–60% EtOAc in n-hexane afforded the product as a mixture of diastereomers. (5.14 g, 59%): TLC R_f 0.25 (silica, 50% EtOAc, n-hexane), ¹H NMR (CDCl₃) δ1.4 (3H, dd), 1.65 (3H, d, J=7 Hz), 2.4 (2H, br s), 3.75 (3H, d), 3.2–3.7 (4H, m), 4.8 (1H, m), 5.2 (1H, m), 5.85 (1H, t), 7.85 (4H,m).

c.) 1-(1-methoxycarbonyl-ethyl)-5-(1-t-butyloxycarbonylamino-ethyl)-2,3,6,7-tetrahydro-1H-azepin-2-one (6b)

To a stirred solution of the above (6b) (5.14 g) in ethanol (150 mL) was added hydrazine mono-hydrate (1.35 mL). The reaction was left stirring at room temperature for 3 days, evaporated to dryness, taken up in CHCl₃, filtered free of insoluble materials and evaporated to dryness. The free amine was dissolved in THF (100 mL) and with stirring, di-t-butyl-dicarbonate (4.8 g) was added. After stirring for 16 h, the reaction was evaporated to dryness. Flash chromatography on silica gel eluted with 50–60% EtOAc in n-hexane afforded product, a mixture of diastereomers, as a thick oil. (3.139, 66%): TLC R_f 0.26 (silica, 50% EtOAc, n-hexane), ¹H NMR (CDCl₃) δ1.25 (3H, d, J=6 Hz), 1.4 (9H, s), 1.45 (3H, d, J=6 Hz), 2.3 (2H, br s), 3.7 (3H, s), 3.2–3.7 (4H, m), 4.1 (1H, m), 5.2 (1H, m), 5.65 (1H, t).

d.) 1-(1-methoxycarbonyl-ethyl)-3-benzyl-5-(1-t-butyloxy-carbonylamino-ethyl)-2,3,6,7-tetrahydro-1H-azepin-2-one (7b)

To a stirred solution of the above (6b) (3.1 g) in dry THF (250 mL) at −78° C. under Ar was added lithium hexamethyldisilazane (19 mL, 1N in THF). After stirring for 30 min benzyl iodide (1.8 mL) was added in one portion. After stirring for 1.5h the reaction was quenched with sat. NH₄Cl, extracted with EtOAc, washed with H₂O, dried over MgSO₄ and evaporated. Flash chromatography on silica gel eluted with 35–60% EtOAc in n-hexane afforded the product as a mixture of diastereomers (2.22 g, 60%) as well as recovered starting material (1.07 g). TLC R_f 0.49 (silica, 40% EtOAc, n-hexane); ¹H NMR (CDCl₃) δ1.2 (3H, dd), 1.4 (9H, s), 1.45 (3H, d), 2.3 (2H, br s), 2.6–3.0 (1H, m), 3.2–3.6 (2H, m), 3.7 (3H, d), 3.9 (3H, m), 4.6 (1H, m), 5.15 (1H, m), 5.4 (1H, br s), 7.3 (5H, s); MS (DCI,NH₃) (M+H)⁺=431.2.

e.) 1-(1-benzyloxycarbonyl-ethyl)-3-benzyl-5-(1-t-butyloxy-carbonylamino-ethyl)-2,3,6,7-tetrahydro-1H-azepin-2-thione (12)

To a stirred solution of the above (7b) (2.2 g) in dry toluene (50 mL) was added at room temperature Lawesson's reagent (1.2 g). The suspension was stirred under Ar at 80° C. for 4h (after 15 min the reaction became clear), evaporated and purified by flash chromatography eluted with 30–40% EtOAc in n-hexane. A fraction (1.78 g) which contained mostly thioamide with some starting material was used in the the next reaction. TLC R_f 0.58 (silica, 40% EtOAc, n-hexane); ¹H NMR (CDCl₃) δ1.1 (3H, dd), 1.4 (9H, s), 1.5 (3H, dd), 2.35 (2H, br s), 2.8–3.2 (1H, m), 3.3–3.6 (1H, m), 3.7 (3H, s), 3.7–4.7 (6H, m), 5.4 (1H, br s), 7.3 (5H, s); MS (DCI,NH₃) (M+H)⁺=447.2.

f.) 1-(1-methoxycarbonyl-ethyl)-3-benzyl-5-(1-t-butyloxycarbonylamino-ethyl)-2,3,6,7-tetrahydro-1H-azepine (13)

To a stirred solution of the above (12) (1.78 g) in CH₂Cl₂ (4 mL) at 0° C. under Ar was added triethyloxonium tetrafluoroborate (3.9 mL 1N in CH₂Cl₂). The reaction was stirred for 5 min at 0° C. then for 45 min at room temperature, evaporated to a foam, dissolved in methanol (6 mL) and cooled to 0° C. NaBH₄ (0.32 g) was then added portionwise with stirring. (exothermic!) The reaction was stirred at 0° C. for 10 min then at room temperature for 2 h, quenched with aqueous 1N HCl (10 mL) and evaporated to dryness. The residue was taken up in EtOAc washed with sat. NaHCO₃, brine, dried over Na₂SO₄ and evaporated. Flash chromatography on silica gel eluted with 30–40% EtOAc in n-hexane afforded product as a mixture of diastereomers (0.7 g) along with unreacted amide (0.3 g). TLC R_f 0.53 (silica, 30% EtOAc, n-hexane); ¹H NMR (CDCl3) δ1.2 (6H, m), 1.4 (9H, s), 2.2–3.0 (9H, m), 3.4 (1H, m), 3.65 (3H, d), 4.1 (1H, m), 4.5 (1H, d, J=5Hz), 5.6 (1H, br s), 7.3 (5H, s); MS (DCI,NH3) (M+H)+ =417.2.

g.) 2-[3-benzyl-5-(1-t-butyloxycarbonylamino-ethyl)-2,3,6,7-tetrahydro-1H-azepin-1-yl]-1-oxo-propyl-valinyl-valine methyl ester (14)

To a stirred solution of the above (13) (0.7 g) in MeOH (10 mL) was added aqueous 1N NaOH (6 mL). After stirring for 16 h, aqueous 1N HCl was added (8 mL) and the reaction evaporated to dryness. After drying under vacuo overnight the residue was taken up in DMF (20 mL) and HCl.H-Val-Val-OMe (0.9 g), HOBt (0.5 g), NEt3 (1.4 mL) and Bop reagent (1.5 g) were added with stirring. The reaction was stirred for 16h and evaporated to dryness. Flash chromatography on silica gel eluted with 45% EtOAc in n-hexane afforded product (14) as a mixture of diastereomers (0.3 g): TLC Rf 0.42 (silica, 50% EtOAc, n-hexane); 1H-NMR (CDCl3) δ1.0 (12H, m) valine γ(CH3)2's, 1.2 (6H, m) alanine CH3's, 1.4 (9H, s) Boc t-butyl, 3.75 (3H, s) methyl ester, 5.6 (1H, br s) olefinic CH, 6.7 (1H, d, J=7 Hz) urethane NH, 7.3 (5H, s) phenyl.

h.) 2-[3-benzyl-5-(1-alanylamino-ethyl)-2,3,6,7-tetrahydro-1H-azepin-1-yl]-1-oxo-propyl-valinyl-valine methyl ester (15)

To the above (14) (0.3 g) was added sat. HCl/dioxane with stirring at room temperature. After stirring for 1 h. the reaction was evaporated to dryness and triturated with ether and filtered to give the di-hydrochloride as a white powder (0.28 g). To the di-hydrochloride in DMF (10 mL) was added NEt3 (0.21 mL) followed by (Boc-Ala)2O, obtained from Boc-alanine (0.3 g) and DCC (0.16 g). The reaction was stirred for 4 h at room temperature and evaporated to dryness. Flash chromatography on silica gel eluted with 60% EtOAc in n-hexane afforded the product (15) as a mixture of isomers (0.27 g, 77%): TLC Rf 0.23 (silica, 60% EtOAc, n-hexane), Rf 0.68 (silica, 5% MeOH, CHCl3); 1H NMR (CDCl3) δ1.0 (12H, m) valine γ(CH3)2's, 1.2–1.4 (9H, m) alanine βCH3's, 1.45 (9H, s) Boc t-butyl, 3.75 (3H, s) methyl ester, 5.6 (1H, br s) olefinic CH, 7.3 (5H, s) phenyl.

i.) 2-[3-benzyl-5-(1-alanylamino-ethyl)-2,3,6,7-tetrahydro-1H-azepinyl]-1-oxo-propyl-valinyl-valine methyl ester (16)

The above Boc-peptide (15) (0.27 g) was treated with 80% TFA in CH2Cl2 with stirring for 30 min and evaporated to dryness. Trituration and filtration from ether gave the title product as a powder (0.23 g). HPLC (PRP-1, 23% CH3CN, 0.1%TFA/0.1% TFA, H2O) of the crude product showed 4 peaks. Preparative HPLC using the same conditions afforded 3 fractions; the first two fractions containing predominately a single peak each in >90% purity and the third fraction a mixture of the last two peaks. All three fractions had identical mass as analyzed by MS (FAB, DTT/DTE) (M+H)+ =586.

EXAMPLE 3

Preparation of 2-[3-benzyl-5-(1-(phenylalanyl)amino-ethyl)-2,3,6,7-tetrahydro-1H-azepin-1-yl]-1-oxo-propyl-valinyl-valine methyl ester a.) 2-[3-benzyl-5-(1-(t-butyloxycarbonyl-phenylalanylamino) -ethyl)-2,3,6,7-tetrahydro-1H-azepin-1-yl]-1-oxo-propyl-valinyl-valine methyl ester This compound was prepared in a manner similar to compound (15) in Example 2 using (Boc-Phe)2O instead of (Boc-Ala)2O. To the di-hydrochloride of compound (14) (100 mg), prepared as in Example 2, in DMF (5 mL) was added NEt3 (47 uL) followed by (Boc-Phe)2O, obtained from Boc-phenylalanine (0.18 g) and DCC (0.07 g). The reaction was stirred for 16 h at room temperature and evaporated to dryness. Flash chromatography on silica gel eluted with 60% EtOAc in n-hexane afforded the product as a mixture of isomers. TLC Rf 0.35 (silica, 60% EtOAc, n-hexane).

b.) 2-[3-benzyl-5-(1-(phenylalanyl)amino-ethyl)-2,3,6,7-tetrahydro-1H-azepin-1-yl]-1-oxo-propyl-valinyl-valine methyl ester The above prepared Boc-peptide was treated with 80% TFA in CH2Cl2 with stirring for 30 min and evaporated to dryness. Trituration and filtration from ether/pet. ether gave the product as a mixture of isomers. HPLC (PRP-1, 30% CH3CN, 0.1% TFA/0.1% TFA, H2O) of the crude product showed 4 peaks. Preparative HPLC using the same conditions afforded 3 fractions; the first fraction containing the first peak, the second fraction containing the second and third peaks and the third fraction a mixture of the last two peaks. All three fractions had identical mass as analyzed by FAB-MS DTT/DTE (M+H)+ =662.3.

EXAMPLE 4

Preparation of 2-[3-benzyl-5-(1-(alanyl-alanyl)amino-ethyl)-2,3,6,7-tetrahydro-1H-azepin-1-yl]-1-oxo-propyl-valinyl-valine methyl ester Substituting Boc-Ala-Ala-OH and a coupling agent such as DCC/HOBt or Bop in place of (Boc-Ala)2O, in the procedure of Example 2, 2-[3-benzyl-5-(1-(alanyl-alanyl)amino-ethyl)-2,3,6,7-tetrahydro-1H-azepin-1-yl]-1-oxo-propyl-valinyl-valine methyl ester is obtained.

EXAMPLE 5

Preparation of 2-[3-benzyl-5-(1-alanylamino-ethyl)-2,3,6,7-tetrahydro-1H-azepin-1-yl]-1-oxo-propyl-valine methyl ester Using HCl.H-Val-OMe in place of HCl.H-Val-Val-OMe in the procedure of Example 2 gives 2-[3-benzyl-5-(1-alanylamino-ethyl)-2,3,6,7-tetrahydro-1H-azepin-1-yl]-1-oxo-propyl-valine methyl ester.

EXAMPLE 6

Preparation of 2-(2-hydroxy-3-benzyl-5-methyl-cyclohept-4-en-1-yl)-1-oxo-ethyl-valinyl valine methyl ester (25)

Compound 25 of Scheme 3 diagrammed hereabove is prepared as follows:

a.) 4-methyl-1-methoxy-1,3-cyclohexadiene (17)

To a mechanically stirred solution of 4-methylanisole (47 g) in ethyl ether (100 mL) and t-butanol (60 g) was condensed dropwise via a cold finger ammonia (500 mL). With vigorous stirring lithium wire (7.7 g) was next added in portions over 15 min during which time the solution became dark blue(slight exotherm). After stirring for 1 h the reaction was slowly quenched with ethanol (~80 mL) over 30 min. The now white reaction was then warmed to room temperature to allow all the ammonia to evaporate. The remaining material was taken up in ether, washed with water, saturated NaCl, dried over Na2SO4 and evaporated on the rotovap (no external heating, the product is extremely volatile). (17); GC RT 6.88 min. (HP 530 mμ×20 m methylsilicone column, He carrier flow rate 20 mL/min., 60° C. isothermal). GC showed 4% starting material remaining ¹H NMR (CDCl₃) δ1.7(3H, s), 2.7(4H, s), 3.5(3H, s), 4.65(1H, br s), 5.4(1H, br s).

b.) 4-methyl-3-cyclohexen-1-one (18)

To the above enol ether (17), without further purification, in ethyl acetate (250 mL) was added with vigorous stirring aqueous 1N HCl (150 mL). The two phase suspension was stirred for 1 h then poured into a separatory funnel. The ethyl acetate phase was removed and the remaining aqueous phase re-extracted one more time with fresh ethyl acetate. The ethyl acetate phases were combined, washed with saturated NaCl, dried over MgSO₄ then evaporated free of solvent to give the product (18) (39.60 g, 94%) as a clear liquid (no external warming, the product will evaporate over if not careful). GC RT 4.29 min. (HP 530 mµ×20 m methylsilicone column, He carrier flow rate 20 mL/min., 60° C. isothermal); TLC R$_f$ 0.41 (5% ethyl acetate, n-hexane); ¹H NMR (CDCl₃) δ1.8 (3H, br s), 2.48(4H, br s), 2.88(2H, br s), 5.5(1H, br s).

c.) 2-benzyl-4-methyl-3-cyclohexen-1-one (19)

To a stirred solution of the above (18) (6.1 g) in dry THF (100 mL) at −78° C. was added a solution of lithium bis-trimethylsilylamide (50 ml, 1N in THF). The solution was stirred for 20 min then benzylbromide (30 mL) was added in one portion. The reaction was stirred for 6 h at −78° C. then allowed to slowly warm to room temperature. After evaporation of the solvent, the remaining mixture was taken up in hexane, washed with saturated NaCl, dried over MgSO₄ and evaporated. The product (19) was obtained by flash chromatography on silica gel eluted with 2.5% ethyl acetate in hexane. (4.15 g, 39%): GC RT 7.29 min. (HP 530 mµ×20 m methylsilicone column, He carrier flow rate 20 mL/min., 100° C., 1 min., 100°–180° C. 10° C./min.; TLC R$_f$0.31 (5% ethyl acetate, n-hexane); ¹H NMR (CDCl₃) δ1.73(3H, br s), 2.2–3.3(7H, m), 5.35(1H, br s), 7.28(5H, m).

d.) t-butyl 2-benzyl-4-methyl-3-cyclohepten-1-one-7-carboxylate (20) and t-butyl-3-benzyl-5-methyl-4-cyclohepten-1-one-2-carboxylate (21)

To a stirred solution of the above ketone (19) (8.18 g) in methylene chloride (18 mL) at −78° C. was added a cold solution of triethyloxonium tetrafluoroborate (28 mL, 1N in CH₂Cl₂). Immediately afterwards t-butyl diazoacetate (4.1 mL) was added and the reaction stirred for 15 min at −78° C. then allowed to slowly warm up in an ice bath. After the cessation of gas evolution (~15 min), the reaction was quenched by the addition of aqueous saturated NaHCO₃ (150 mL) and stirred an additional 15 min. The organic phase was removed and the aqueous phase re-extracted with fresh CH₂Cl₂. The CH₂Cl₂ phases were then combined, dried over MgSO₄ and evaporated. The product (20) was obtained by silica gel chromatography (5.0×100 cm) eluting with 2.5% ethyl acetate in n-hexane (2.11 g, 17.4%). Another later eluting fraction was obtained which corresponded to the other regioisomer (21) (3.71 g, 30.6%).

(20): TLC R$_f$ 0.57 (10% ethyl acetate, n-hexane); MS DCI/NH₃ (M+NH₄)⁺=332; ¹H NMR (CDCl₃) δ(M=major, m=minor) 1.3M and 1.43m(9H, 2s), 1.67M and 1.72m(3H, 2s), 2.0–2.5(4H, m), 2.77(1H, 2dd) major and minor benzylic CH, 3.12M and 3.27m(1H, 2dd) benzylic CH, 3.39M and 3.53m(1H, 2dd) malonyl CH, 3.69m and 4.08M(1H, 2 br s) allylic CH, 5.04M and 5.16m(1H, 2 br s) vinyl CH, 7.22(5H, s) phenyl.

(21): TLC R$_f$ 0.53 (10% ethyl acetate, n-hexane); MS DCI/NH₃ (M+NH₄)⁺=332; ¹H NMR (CDCl₃) δ1.34m and 1.49M(9H, s and d), 1.68M and 1.77m(3H, 2s), 2.2–3.1(6H, m), [major benzylic CH₂ at δ2.60(1H, dd) and 2.79(1H, dd)], 3.3(1H, br s) allylic CH, 3.48m and 3.53M(1H, 2d) malonyl CH, 5.28M and 5.43m(1H, 2d) vinyl CH, 7.32(5H, s) phenyl.

e.) methyl (1-t-butyloxycarbonyl-2-oxo-3-benzyl-5-methyl-cyclohept-4-en-1-yl)-ethanoate (22)

To a stirred solution of the above β-keto ester (20) (2.0 g) in dry THF (50 mL) under argon at room temperature was added NaH (0.4 g, 60% dispersion in oil). After 15 min methyl bromoacetate (3 mL) was added and the reaction refluxed at 80° C. under argon for 16 h. The reaction was quenched with aqueous 1N HCl and extracted with ethylacetate, washed with saturated NaCl, dried over MgSO₄ and evaporated. The product was obtained by flash chromatography on silica gel eluting with 5% ethyl acetate in n-hexane (1.35 g). Unreacted starting material (1.12 g) was also recovered and resubjected to the above reaction to obtain additional product (0.91 g, 92% overall): TLC R$_f$0.16 (5% ethyl acetate, n-hexane); ¹H NMR (CDCl₃) δ1.44 (9H, s) CO₂t-Bu, 1.64 (3H, s) allylic CH₃, 3.6(3H, s) CO₂CH₃, 4.03(1H, br s) allylic CH, 5.05(1H, br s) vinyl CH, 7.29 (5H, s) phenyl.

f.) methyl (2-oxo-3-benzyl-5-methyl-cyclohept-4-en-1-yl)-ethanoate (23)

To a stirred solution of the above di-ester (22) (1.35 g) in CH₂Cl₂ (20 mL) was added trifluoroacetic acid (80 mL). After stirring for 45 min the reaction was evaporated to dryness and re-evaporated twice with fresh toluene to remove any residual TFA. The oil which remained was then taken up in toluene (100 mL) and refluxed under Ar for 1 h. The product (23) was obtained after evaporation and purification by flash chromatography on silica gel eluted with 10% ethyl acetate in n-hexane (0.85 g, 85%).

(23): TLC R$_f$ 0.25 (10% ethyl acetate, n-hexane); ¹H NMR (CDCl₃) δ1.71(3H, s) allylic CH₃, 3.6(3H, s) CO₂CH₃, 3.8(1H, br s) allylic CH, 5.12m and 5.20M(1H, br s and d) vinyl CH, 7.23 (5H, s) phenyl.

g.) 2-(2-oxo-3-benzyl-5-methyl-cyclohept-4-en-1-yl)-1-oxo-ethyl-valinyl valine methyl ester (24)

To the above keto ester (23) (0.51 g) in 4:1 dioxane, water (10 mL) was added LiOH.H₂O (82 mg). The reaction was stirred overnight at room temperature, evaporated, taken up in ethyl acetate washed with aqueous 1N HCl, saturated NaCl, dried over MgSO₄ and evaporated to give the crude keto acid. The acid was dissolved in DMF (10 mL) to which was added HCl.Val-Val-OMe (0.51 g), triethylamine (1.5 mL), hydroxybenzotriazole (0.48 g) followed by Bop reagent (1.57 g). The reaction was stirred overnight at room temperature and evaporated to dryness. The product (24) was obtained as a mixture of diastereomers by flash chromatography on silica gel eluted with 50% ethyl acetate in n-hexane. (0.44 g, 51%) (24); TLC R$_f$0.24 and 0.26 (40% ethyl acetate, n-hexane); ¹H NMR (CDCl₃) δ0.8–1.0(12H, m) Val γ(CH₃)2's, 1.7(3H, s) allylic CH₃, 3.7(3H, s) CO₂CH₃, 3.8 (1H, br s) allylic CH, 4.55 (2H, dd), 5.15 (1H, m) vinylic CH, 7.25 (5H, s) phenyl.

h.) 2-(2-hydroxy-3-benzyl-5-methyl-cyclohept-4-en-1-yl)-1-oxo-ethyl-valinyl valine methyl ester (25)

To the above keto-peptide (24) (0.44 g) in ethanol (20 mL) with stirring at room temperature was added NaBH₄ (69 mg) in one portion. After stirring for 30 min the reaction was quenched by the addition of aqueous 1N HCl (50 mL). The reaction was extracted with ethyl acetate, washed with saturated NaCl, dried over MgSO$_4$ and evaporated to dryness. The title compound was obtained as a mixture of diastereomers by flash chromatography on silica gel eluted with 60% ethyl acetate in n-hexane then by gravity chromatography in the same system. TLC R$_f$ 0.31 and 0.36 (60% ethyl acetate, n-hexane); MS (DCI/NH$_3$) (M+H)$^+$=487; $^1$H NMR (CDCl$_3$)δ0.8–1.0(12H, m) Val γ(CH$_3$)2's, 1.7 (3H, s) allylic CH$_3$, 3.72 (3H, s) CO$_2$CH$_3$, 5.18m and 5.08(1H, br s) vinylic CH, 7.30(5H, s) phenyl.

EXAMPLE 7

Preparation of 2-(2-hydroxy-3-benzyl-5-methyl-cyclohept-5-en-1-yl)-1-oxo-ethyl-valinyl valine methyl ester Using the procedure of Example 6 as outlined in Scheme 3, except that the benzylation step 6(c) (with benzyl bromide) is carried out after the ring expansion step 6(d), the title compound is obtained.

EXAMPLE 8

Preparation of 2-(2-hydroxy-3-benzyl-5-t-butyl-cyclohept-4-en-1-yl)-1-oxo-ethyl-valinyl valine methyl ester Using 4-t-butyl-anisole in place of 4-methyl-anisole in the procedure of Example 6 yields the title compound.

EXAMPLE 9

Preparation of 2-(2-hydroxy-3-(4-imidazolyl) methyl-5-methyl-cyclohept-4-en-1-yl)-1-oxo-ethyl-valinyl valine methyl ester Using (4-imidazolyl)methyl bromide in place of benzyl bromide in the procedure of Example 6 yields the title compound.

EXAMPLE 10

Preparation of 2-(5-[(1S)-1-alanylamino-ethyl]-3-benzyl-2-hydroxy-cyclohept-4-en-1-yl)-1-oxo-ethyl-valinyl-valine methyl ester (41)

Compound 41 of Scheme 4 outline hereabove is prepared as follows:

a.) 4-(S)-benzyl-3-(4-methoxy)phenylacetyl-2-oxazolidinone (26)

To a solution of 4-methoxyphenylacetic acid (50 g) in dry toluene (10 mL) was added oxalylchloride (50 mL). The reaction was stirred at room temperature for 16 h, evaporated to dryness and re-evaporated from toluene several times to remove any excess oxalyl chloride. This crude acid chloride (57.2 g) was next added to a solution of the lithium salt of (S)-4-benzyl-2-oxazolidinone at −78° C. prepared from a solution of (S)-4-benzyl-2-oxazolidinone (60 g) in dry THF (700 mL) to which was added a solution of n-butyllithium (130 mL, 2.5N in n-hexane) at −78° C. with stirring for 10 min. After stirring for an additional 1 h at −78° C. the reaction was quenched with saturated NH$_4$Cl, extracted with ethyl acetate, washed with saturated NaCl, dried over MgSO$_4$ and evaporated. The product (26) was obtained by crystallization in ethyl acetate, n-hexane (67.74 g, 70%): TLC R$_f$ 0.31 (20% ethyl acetate, n-hexane); $^1$H NMR (CDCl$_3$) δ2.77 (1H, dd), 3.29(1H, dd), 3.8(3H, s), 4.19(2H, d, J=6 Hz), 4.27(2H, s), 4.7(1H, m), 6.85–7.45(9H, m).

b.) (2S, 4S)-4-benzyl-3-(1-oxo-2-(4-methoxy-phenyl)-propyl)-2-oxazolidinone (27)

To a stirred solution of the above chiral amide (26) (67.6 g) in dry THF (500 mL) at −78° C. under Ar was added a solution of lithium bis-trimethylsilylamide (223 mL, 1N in THF). After stirring for 15 min methyl iodide (21 mL) was added in one portion. The reaction was stirred for 1 h at −78° C. then allowed to warm to 0° C. for 1 h, quenched with saturated NH$_4$Cl, extracted with ethyl acetate, washed with saturated NaCl, dried over MgSO$_4$ and evaporated. The product (27) was obtained by flash chromatography on silica gel eluted with 20% ethylacetate in n-hexane (56.22 g, 80%). Analytical HPLC showed that the diastereomers were separable with the crude reaction giving a diastereomeric excess of ~88% and the product obtained by flash chromatography having a de of >95%. An optically pure sample (27) can be obtained by crystallization from ethyl acetate/n-hexane: R$_f$ 0.49 (20% ethyl acetate, n-hexane); HPLC (Zorbax 4.6×250 mm, silica gel, 1.5 mL/min.) RT 8.87 min; $^1$H NMR (CDCl$_3$) δ1.55(3H, d, J=7 Hz), 2.9(1H, m), 3.4(1H, dd), 3.8(3H, s), 4.12 (2H, m), 4.62 (1H, m), 5.15 (1H, q), 7.15 (4H, q), 7.35 (5H, br s).

c.) (2S)-2-(4-methoxy-phenyl)-propanoic acid (28)

To a mechanically stirred solution of the above amide (27) (56.2 g) in THF (750 mL) and H$_2$O (250 mL) at 0° C. was added a solution of lithium hydroperoxide prepared by adding a solution of LiOH.H$_2$O (10.4 g) in H$_2$O (250 mL) to 30% H$_2$O$_2$ (84 mL). After stirring for 1 h at 0° C. the excess peroxide was destroyed by the slow addition of a solution of Na$_2$SO$_3$ (103 g) in H$_2$O (500 mL) (exothermic!). After removing most of the THF by evaporation the remaining solution was washed with CH$_2$Cl$_2$ twice to remove recoverable (S)-4-benzyl-2-oxazolidinone, acidified to pH ~2 with 3N HCl and extracted twice with ethyl acetate to isolate the product. The ethyl acetate phases were combined, washed with saturated NaCl, dried over MgSO$_4$ and evaporated to give TLC pure product, (28) (29.87 g, 100%). TLC R$_f$ 0.49 (95:4:1 CHCl$_3$:MeOH:HOAc) R$_f$ 0.33 streaks (98:2 CHCl$_3$:MeOH); $^1$H NMR (CDCl$_3$)δ1.5(3H, d, J=7 HZ), 2.25 (2H, br s), 2.78 (3H, s), 4.08 (1H, q), 7.15 (4H, q).

d.) (1S) -N-benzyloxycarbonyl-1-(4-methoxy-phenyl)ethylamine (29)

To a stirred solution of the above acid (28) (29.87 g) in dry toluene (300 mL) at room temperature fitted with a reflux condenser under Ar was added triethylamine (26 mL) followed by diphenylphosphorylazide (38 mL). The reaction was then placed into an oil bath at 80° C. and stirred till gas evolution ceased (~30 min). Benzyl alcohol (17 mL) was next added and the reaction stirred for 3 h at 80° C., evaporated, taken up in ethyl acetate, washed with aqueous 1N Na$_2$CO$_3$, aqueous 1N HCl, saturated NaCl, dried over MgSO$_4$ and evaporated. The product (29) was obtained by flash chromatography on silica gel eluted with 20% ethyl acetate in n-hexane. (42.87 g, 91%): TLC R$_f$ 0.36 (CHCl$_3$) R$_f$ 0.39 (20% ethyl acetate, n-hexane).

e.) (1S)-1-(4-methoxy-phenyl)-ethylamine (30)

A solution of the above (29) (42.8 g) in methanol (300 mL) was hydrogenated over 5% Pd on carbon (~2 g) at 50 psi H$_2$ for 4 h in a Parr shaker. The product (30) was obtained after filtration of the catalyst through Celite®, rinsing with fresh methanol and evaporation (22.9 g, 100%). GC RT 4.68 min (HP 530 mμ×20 m methylsilicone column, He carrier flow rate 20 mL/min, 100° C. isothermal); $^1$H NMR (CDCl$_3$) δ1.37 (3H, d, J=7 Hz), 2.25(2H, br s), 2.78(3H, s), 4.08(1H, q), 7.15(4H, q).

f.) 1-[(1S)-1-aminoethyl]-4-methoxy-1,4-cyclohexadiene (31)

To a mechanically stirred solution of the above amine (30) (24 g) in dry THF (200 mL) and t-butanol (12 g) was condensed via a cold finger ammonia (800 mL). Lithium wire (3.1 g) was next added piece-wise over 15 min and the now dark blue reaction stirred for 1 h. Ethanol was then dripped into the reaction very slowly over 1 h until the reaction turned blue. The reaction was then allowed to warm to room temperature, with external warming, to allow the ammonia to evaporate. The remaining mixture was taken up in ethyl ether, washed with H$_2$O, dried over Na$_2$SO$_4$ and evaporated to yield the titled product (31): GC RT 5.63 min (HP 530 mμ×20 m methylsilicone colunm, He carrier flow rate 20 mL/min, 100° C. isothermal).

g.) 1-[(1S)-1-(1-benzyloxycarbonylamino-ethyl]-4-methoxy-1,4-cyclohexadiene (32)

To a stirred solution of the above diene (31) in THF (250 mL) was added in one portion N-(benzyloxycarbonyloxy) -succinimide (40 g) (slightly exothermic) followed by after 15 min triethylamine (23 mL). The reaction was stirred for 16 h at room temperature, evaporated, taken up in ethyl acetate, washed with 1N Na$_2$CO$_3$, saturated NaCl, dried over MgSO$_4$ and evaporated to give crude product (32). TLC R$_f$ 0.26 (10% ethyl acetate, n-hexane); $^1$H NMR (CDCl$_3$) δ1.24 (3H, d, J=7 Hz), 2.73(4H, br s), 3.55(3H, s), 4.27(1H, q), 4.64(1H, br s), 4.78(1H, br d), 5.12(2H, s), 5.64(1H, br s), 7.38 (5H, s).

h.) 4-[(1S)-1-benzyloxycarbonylamino-ethyl]-cyclohex-3-en-1-one (33)

To a vigorously stirred solution of the above diene (32) (44.2 g) in ethyl acetate (250 mL) was added aqueous 1N HCl (250 mL). After stirring for 1 h the ethyl acetate phase was removed, washed with saturated NaCl, dried over MgSO$_4$ and evaporated. The product (33) was obtained by flash chromatography on silica gel eluted with 35% ethyl acetate in n-hexane (39.69 g, 91%). TLC R$_f$ 0.51 (30% ethyl acetate, n-hexane); $^1$H NMR (CDCl$_3$)δ1.25(3H, d, J=7 Hz), 2.44(4H, br s), 2.88(2H, br s), 4.35(1H, q), 4.95(1H, br d), 5.13(2H, s), 5.72(1H, t), 7.38 (5H, s).

i.) 2-benzyl-4-[(1S)-1-benzyloxycarbonylamino-ethyl]-cyclohex-3-en-1-one (34)

To a stirred solution of the above ketone (33) (14.93 g) in dry THF (200 mL) at −78° C. under Ar was added a solution of lithium bis-trimethylsilylamide (55 mL, 1N in THF). After stirring for 20 min benzylbromide (35 mL) was added and the reaction stirred for an additional 6 h at −78° C. then allowed to slowly warm to room temperature. The reaction was taken up in ethyl acetate, washed with 1N HCl, saturated NaCl, dried over MgSO$_4$ and evaporated. The product (34) was obtained by flash chromatography on silica gel eluted with 20 to 25% ethyl acetate in n-hexane (6.09 g, 31%): TLC R$_f$ 0.17 (20% ethyl acetate, n-hexane); $^1$H NMR (CDCl$_3$) δ1.12 (3H, d, J=7 Hz), 2.0–3.2 (7H, m), 4.18(1H, q), 5.1(2H, s), 5.33(1H, dd), 5.55(1H, br s), 7.22 (5H, m), 7.32 (5H, s).

j.) methyl (5-[(1S)-1-benzyloxycarbonylamino-ethyl]-3-benzyl-2-oxo-cyclohept-4-en-1-yl)-ethanoate (35) and methyl (5-[(1S)-1-benzyloxycarbonylamino-ethyl]-7-benzyl-2-oxo-cyclohept-5-en-1-yl)-ethanoate (36)

To a stirred solution of the above alkylated ketone (34) (7.8 g) in CH$_2$Cl$_2$ (24 mL) at −78° C. under Ar was added a solution of triethyloxonium tetrafluoroborate (37 mL, 1N in CH$_2$Cl$_2$). Immediately afterwards t-butyl diazoacetate (5.4 mL) was added and the reaction stirred for 10 min at −78° C. then allowed to warm to 0° C. in an ice bath until gas evolution subsided (∼15 min). The reaction was quenched with aqueous saturated NaHCO$_3$ (100 mL) and stirred for 15 min. The CH$_2$Cl$_2$ phase was removed and the aqueous phase re-extracted with fresh CH$_2$Cl$_2$. The combined CH$_2$Cl$_2$ phases were then dried over MgSO$_4$ and evaporated. Crude ring expanded product was obtained by flash chromatography on silica gel eluted with 20% ethyl acetate in n-hexane (5.73 g, 89%). TLC R$_f$ 0.33 and 0.30 (20% ethyl acetate, n-hexane).

To a stirred solution of the above (5.73 g) in dry THF (100 mL) at room temperature under Ar was added NaH (0.7 g, 60% dispersion in oil). After stirring for 15 min methyl bromoacetate (5.0 mL) was added in one portion and the reaction refluxed for 24 h. The reaction was then quenched with aqueous 1N HCl and extracted with ethyl acetate. The ethyl acetate phase was washed with saturated NaCl, dried over MgSO$_4$ and evaporated. Crude alkylated product was obtained by flash chromatography on silica gel eluted with 25–30% ethyl acetate in n-hexane (5.15 g, 78%). TLC R$_f$ 0.37 and 0.42 (30% ethyl acetate, n-hexane).

To a stirred solution of the above diester (5.15 g) in CH$_2$Cl$_2$ (40 mL) was added trifluoroacetic acid (160 mL). The reaction was stirred at room temperature for 45 min then evaporated to dryness. The crude acid was reevaporated from fresh toluene twice to remove trace amounts of trifluoroacetic acid then taken up in toluene (150 mL) and refluxed for 1 h under Ar. Products (35) and (36) were obtained after evaporation by flash chromatography on silica gel eluted with 30% ethyl acetate in n-hexane. (2.6 g, 62%). Gravity chromatography (silica gel, 25% ethyl acetate/n-hexane) yielded the pure regioisomers as a mixture of diastereomers.

(35): TLC R$_f$ 0.43 (30% ethyl acetate, n-hexane); $^1$H NMR (CDCl$_3$) δ1.14 (3H, d, J=7 Hz), 1.5–3.3(9H, m), 3.57(3H, s), 3.7 (1H, m), 4.15 (1H, m), 5.1 (2H, s ), 5.5 (1H, d), 7.23 (5H, s), 7.38(5H, s).

(36): TLC R$_f$ 0.39, 0.35 (30% ethyl acetate, n-hexane); $^1$H NMR (CDCl$_3$) δ1.2 (3H, m), 2.0–3.1 (9H, m), 3.55 (1H, m), 3.67 (3H, s), 4.12 (1H, m), 5.1 (2H, s), 5.3–5.7 (1H, m), 7.28(5H, s), 7.36(5H, s).

k.) (5-[(1S)-1-benzyloxycarbonylamino-ethyl]-3-benzyl-2-oxo-cyclohept-4-en-1-yl)-ethanoic acid (37)

To a stirred solution of the above ester (35) (1.2 g) in dioxane (12 mL) was added a solution of NaOH (5.3 mL, 1N in H$_2$O). After stirring for 4 h at room temperature 1N HCl (5.3 mL) was added and the reaction extracted with ethyl acetate, washed with saturated NaCl, dried over MgSO$_4$ and evaporated. The product (37) was obtained by flash chromatography (silica gel, 98:2:0.1 CHCl$_3$:MeOH:HOAc) (1.0 g, 86%). TLC R$_f$ 0.53 (95:4:1 CHCl$_3$:MeOH:HOAc); MS DC I/NH$_3$(M+H)+ =436.3; $^1$H NMR (CDCl$_3$) δ1.13(3H, d, J=7 Hz ), 1.6–3.3 (9H, m), 3.65 (1H, m), 4.1 (1H, br m), 5.1 (2H, s), 5.45(1H, d), 7.2(5H, s), 7.35(5H, s), 10.65 (1H, br s).

l.) 2-(5-[(1S)-1-benzyloxycarbonylamino-ethyl]-3-benzyl-2-oxo-cyclohept-4-en -1-yl)-1-oxo-ethyl-valinyl-valine methyl ester (38)

To a stirred solution of the above acid (37) (1.0 g) in dimethylformamide (20 mL) was added hydroxybenzotriazole (0.62 g), HCl.Val-Val-OMe (0.67 g), triethylamine (1.93 mL) followed by Bop reagent (1.93 g). After stirring at room temperature for 16 h the reaction was evaporated to dryness and flash chromatographed on silica gel eluted with 60% ethyl acetate in n-hexane to give the titled product (38) (0.95 g, 57%). TLC $R_f$ 0.48, 0.41 (60% ethyl acetate, n-hexane) $R_f$ 0.40, 0.37 (97:3 CHCl$_3$:MeOH); MS DCI/NH$_3$ (M+H)+ =648.5; $^1$H NMR (CDCl$_3$) δ0.8–1.0(12H, m) Val γ(CH$_3$)$_2$'s, 1.12(3H, d, J=7 Hz) Ala CH$_3$, 3.7(3H, s) CO$_2$CH$_3$, 5.1(2H, s) Cbz CH$_2$, 5.4(1H, d) vinyl CH, 7.22(5H, s) phenyl, 7.46(5H, s) Cbz phenyl.

m.) 2-(5-[(1S)-1-benzyloxycarbonylamino-ethyl]-3-benzyl-2-hydroxy-cyclohept-4-en-1-yl)-1-oxo-ethyl-valinyl-valine methyl ester (39)

To a stirred solution of the above (38) (0.47 g) in ethanol (15 mL) was added at room temperature NaBH$_4$(55 mg). After stirring for 30 min the reaction was carefully quenched with acetone then aqueous 1N HCl. The reaction was extracted with ethyl acetate, washed with saturated NaCl, dried over MgSO$_4$ and evaporated. The product (39) was obtained as a mixture of isomers by flash chromatography on silica gel eluted with 50% CHCl$_3$ in ethyl acetate (0.42 g, 89%). TLC $R_f$ 0.36, 0.33 (97:3 CHCl$_3$:MeOH); MS DCI/NH$_3$ (M+H)+ =650.4.

n.) 2-(5-[(1S)-1-(t-butyloxycarbonylalanyl)amino-ethyl]-3-benzyl-2-hydroxy-cyclohept-4-en-1-yl)-1-oxo-ethyl-valinyl-valine methyl ester (40)

To the above alcohol (39) (0.31 g) was added, with stirring under Ar, anisole (2 drops) followed by a solution of 30% HBr in acetic acid (15 mL). After stirring for 30 min at room temperature the reaction was evaporated and re-evaporated several times from toluene to remove any excess acetic acid. The remaining orangish solid was left under vacuo overnight (0.32 g). To the crude HBr salt in dimethylformamide (10 mL), with stirring at room temperature, was added triethylamine (134 mL) followed by a solution of (Boc-Ala)$_2$O [made from Boc-Ala-OH (0.54 g) and dicyclohexylcarbodiimide (0.3 g) in CH$_2$Cl$_2$ (20 mL) with stirring at room temperature for 30 min followed by filtration through Celite®and concentration] in dimethylformamide (10 mL). After stirring at room temperature for 5 h the reaction was evaporated to dryness. The product was obtained as a mixture of isomers by flash chromatography (silica gel, CHCl$_3$ followed by 98:2 CHCl$_3$:MeOH): (0.29 g, 88%). This product was found by MS (DCI/NH$_3$) (M+H)+ =729.4 to be almost entirely the O-acetylated product, presumably from acetic anhydride in the HBr/HOAc, and had to be saponified with aqueous 1N NaOH in MeOH and reesterified with CH$_2$N$_2$ in ether/MeOH to give the titled product (40). TLC $R_f$ 0.33, 0.35 (95:5 CHCl$_3$:MeOH); MS (DCI/NH$_3$) (M+H)+687; $^1$H NMR (CDCl$_3$)δ0.8–1.0(12H, m) Val γ(CH$_3$)$_2$'s, 1.0–1.4(6H, 2d) Ala CH$_3$'s, 1.45(9H, s) Boc, 3.7(3H, s) CO$_2$CH$_3$, 7.28(5H, s) phenyl.

o.) 2-(5-[(1S)-1-(alanyl)amino-ethyl]-3-benzyl-2-hydroxy-cyclohept-4-en-1-yl)-1-oxo-ethyl-valinyl-valine methyl ester (41)

To a stirred solution of 30 mg of (40) in CH$_2$Cl$_2$ (1 mL) was added trifluoroacetic acid (10 mL). After stirring for 45 min the reaction was evaporated to dryness, triturated with ether, filtered and dried under vacuum to give the title compound (41) as a mixture of isomers (24rag, 75%).

EXAMPLE 11

Preparation of (2S) -t-butyl 2-(5,7-dioxo-6-benzyl-4-[(1R)-1-(benzyloxycarbonylalanyl)amino-ethyl]-hexahydro-1H, 4H-1,4-diazepin-1-yl)-propanoate (49)

Compound 49 of Scheme 5 outlined hereabove is prepared as follows:

a.) 2-2-dimethyl-4,6-dione-5-benzyl-1,3-dioxane (42)

Meldrum's acid (14.4 g, 100 mmol) was dissolved in 250 ml of methanol. Borane-dimethylamine (CH$_3$)$_2$NH.BH complex (6.04 g, 102.5 mmol) was added, followed by 20 mL of benzaldehyde (20.88 g; 196.8 mmol). The reaction was kept stirring vigorously, followed by an additional 10 mL of benzaldehyde. The reaction was poured into 600 mL of ice-water and acidified with concentrated hydrochloric acid. After waiting a few minutes a white precipitate formed. The precipitate was collected in a sintered glass funnel and dried under vacuum overnight to give (42) (22.4 g, 96%). $^1$H NMR (CDCl$_3$) δ7.30 (s, 5H), 3.80 (t, 1H), 3.47 (d, 2H); 1.67 (s, 3H), 1.47 (s, 3H).

b.) benzyl 2-benzyl malonate (43)

The benzylated Meldrum's acid (42) (22.40 g, 95.6 mmol) was dissolved in toluene. Benzyl alcohol (20 mL; 20.9 g; 193.3 mmol) was added and the reaction was heated to reflux overnight. The reaction was evaporated and taken up in 1N sodium carbonate solution and extracted with ether (2×). The solution was acidified and extracted with ether (2×). The ether was dried over anhydrous magnesium sulfate, filtered and evaporated to yield (43) an amber colored oil (20.9 g, 77%). $^1$H NMR (CDCl$_3$)δ10.97 (s, 1H), 7.27–7.20 (m, 10H), 5.10 (s, 2H), 4.77 (t, 1H), 3.27 (d, 2H).

c.) N-benzyloxycarbonyl,N-(2-oxo-ethyl)-(S)-alanine t-butyl ester (44)

Benzyloxycarbonyl-L-alanine (15.0 g) (67.2 mmol) was dissolved in methylene chloride with about 1 mL of concentrated sulfuric acid. Isobutylene was added via a dry-ice, cold finger trap. The solution was allowed to warm to room temperature and left stirring overnight. The solution was charged with isobutylene again and left stirring overnight. The solution was extracted with 0.8N aqueous sodium bicarbonate, dried over anhydrous magnesium sulfate, filtered and evaporated under vacuum to give benzyloxycarbonyl-L-alanine t-butyl ester. 1H NMR (CDCl$_3$) δ7.35 (s, 5H), 5.12 (s, 2H), 4.23 (m, 2H), 1.45–1.30 (s/d, 12H).

Benzyloxycarbonyl-L-alanine t-butyl ester (10.0 g, 35.8 mmol) was dissolved in dry THF. Allyl iodide (7.4 mL, 78.8 mmol) was added followed by sodium hydride (1.80 g, 45.0 mmol). The reaction was left stirring at room temperature overnight. The reaction was evaporated and taken up in ethyl acetate. It was extracted with water and treated with sodium metabisulfite. The ethyl acetate was extracted with 1N aqueous sodium carbonate, dried over anhydrous magnesium sulfate, filtered and evaporated under vacuum. The crude product was flash chromatographed (silica gel, hexane followed by hexane:ethyl acetate 95:5) to give N-benzyloxycarbonyl, N-allyl-L-alanine t-butyl ester (6.8 g, 60%). $^1$H NMR (CDCl$_3$) δ7.33 (s, 5H), 6.17–5.67 (m, 1H), 5.20 (d, 4H), 1.75–1.70 (s/d, 12H).

N-benzyloxycarbonyl, N-allyl-L-alanine t-butyl ester (6.8 g, 21.37 mmol) was dissolved in methanol. The solution was cooled in an acetone/dry-ice bath. Ozone was bubbled through the solution for about 20 min until the solution turned a light blue color. Dimethylsulfide (3.6 mL, 3.34 g, 48.9 mmol) was added after the solution was flushed with argon. The reaction was flash chromatographed (silica gel, hexane:ethyl acetate 95:5) to yield the titled product (44) (6.1 g, 89%). $^1$H NMR (CDCl$_3$) δ9.67 (s, 1H), 7.35 (s, 5H), 5.20 (s, 2H), 5.07–4.60 (m, 1H) δ3.97 (s, 2H), 1.77–1.67 (s/d, 12H).

d.) (R)-alanine amide hydrochloride (45)

Boc-D-Alanine (5.0 g) (26.43 mmol) was dissolved in dry THF (100 mL). Triethylamine (4 mL, 2.91 g, 28.76 mmol) was added, followed by ethyl chloroformate (2.5 mL, 2.951 g, 27.19 mmol). The solution was left stirring in a carbon tetrachloride/dry-ice cold bath for about 30 min. Concentrated ammonium hydroxide (5 mL, 74.0 mmol) was added and the solution was stored in the refrigerator overnight. The reaction was evaporated under vacuum and the residue taken up in ethyl acetate. The ethyl acetate was extracted with sodium carbonate and water, dried over anhydrous magnesium sulfate, filtered and evaporated. The residue was treated with saturated hydrochloric acid/dioxane for 1 hour at room temperature. The dioxane was evaporated under vacuum, the residue taken up in a small amount of methanol and precipitated with diethyl ether to yield the title compound (45) (2.5 g, 76%).

e) N-benzyloxycarbonyl,N-(2-[(1R)-1-aminocarbonyl-ethyl]amino-ethyl)-(S)-alanine t-butyl ester (46)

The D-alanine amide hydrochloride, (45) (2.5 g) (20.18 mmol) was dissolved in methanol, followed by the aldehyde (44) (3.30 g, 10.27 mmol) and triethylamine (1.40 mL, 1.0 g, 10.07 mmol). Sodium cyanoborohydride (0.86 g, 13.7 mmol) was added and the solution was kept stirring at room temperature overnight. The solution was evaporated under vacuum. The residue was taken up in chloroform:methanol (98:2) and flash chromatographed silica gel to yield the titled product (46): (2.48 g, 61%). 1H-NMR CDCl$_3$) δ7.33 (s, 5H), 6.00 (br s, 1H), 5.20 (d, 2H), 4.67–3.00 (m, 4H), 2.77 (t, 2H), 1.83–1.23 (s/m, 13H).

f.) N-carbobenzyloxy,N-[2-(N'-[(1R)-1-aminocarbonyl-ethyl], N'-[2-benzyloxycarbonyl-2-benzyl-1-oxoethyl])amino-ethyl]-(S)-alanine t-butyl ester (47)

Benzyl 2-benzyl malonate (43) (6 g, 21.1 mmol) was dissolved in toluene and excess oxalyl chloride. The reaction was kept stirring in an oil bath kept at about 35° C. overnight. The reaction was evaporated and the residue was dried under vacuum to give the acid chloride of benzyl 2-benzyl malonate. $^1$H NMR (CDCl$_3$) δ7.23–7.17 (m, 10H),5.07 (s, 2H), 4.10 (t, 1H), 3.23 (d, 2H).

The secondary amine (46) (2.48 g, 6.3 mmol) was dissolved in chloroform. Pyridine (1.10 mL, 1.08 g, 13.65 mmol) was added, followed by the acid chloride (3.9 g, 12.9 mmol) in toluene. The reaction was left stirring at room temperature overnight. The reaction was evaporated under vacuum and the residue taken up in ethyl acetate. It was extracted with 0.8N aqueous sodium bicarbonate (2×), 1.0N aqueous hydrochloric acid (2×) and brine (1×). It was dried over anhydrous magnesium sulfate, filtered and evaporated. The residue was chromatographed (silica gel, hexane:ethyl acetate 9:1 followed by pure ethyl acetate) to yield the titled product (47): (1.6 g, 40%): $^1$H NMR (CDCl$_3$) δ7.37 (s/m), 5.20 (m), 3.67–3.00 (m), 1.57–1.00 (m).

g.) (2S) -t-butyl 2-(5, 7-dioxo-6-benzyl-4-[(1R)-1-aminocarbonyl-ethyl]-hexahydro-1H, 4H-1,4-diazepin-1-yl)-propanoate (48)

N-carbobenzyloxy, N-[2-(N'-[(1R)-1-aminocarbonyl-ethyl]), N'-[2-benzyloxycarbonyl-2-benzyl-1-oxo-ethyl])amino-ethyl]-(S)-alanine t-butyl ester (47) (1.6 g, 2.51 mmol) was dissolved in methanol and transferred to a Parr vessel. About 1 g of 10% palladium on carbon was added and the vessel was put on the Parr apparatus with about 50 psi of hydrogen. When the reaction was completed, the palladium on carbon was removed by filtration through Celite ® and the solvents were evaporated under vacuum and the residue was dried under vacuum. The residue was dissolved in dimethylformamide (500 mL) and cooled in an acetone/dry-ice bath at −78° C. Diphenylphosphorylamide (1.1 mL.; 1.4 g, 5.1 mmol) was added, followed by solid sodium bicarbonate (1.05 g, 12.55 mmol). The solution was kept stirring at −78° C. for about 1 h then stored in the refrigerator. After 3 days, the dimethylformamide was evaporated under vacuum and the residue dried under vacuum. The residue was dissolved in chloroform and flash chromatographed (silica gel, chloroform:methanol 97:3) to yield the titled product (48) (86 g, 82%). $^1$H NMR (CDCl$_3$) δ7.60 (S), 6.00 (br s), 5.5–3.0 (m), 1.72–1.17 (s/m); MS (DCI/NH$_3$) (M+H)$^+$418.

h.) (2S) -t-butyl 2-(5, 7-dioxo-6-benzyl-4-[(1R)-1-(benzyloxycarbonylalanyl)amino-ethyl]-hexahydro-1H,4H-1,4-diazepin-1-yl)-propanoate (49)

The cyclized primary amide (48) (204.5 rag, 0.49 mmol) was dissolved in 5 mL of acetonitrile:water (4:1) and stirred at room temperature. [Bis (trifluoroacetoxy)iodo]benzene (0.31 g, 0.72 mmol) was added and the reaction was kept stirring at room temperature, under argon. After 5 h, the stirring bar was removed and washed with methanol. The solvents were removed under vacuum. The residue was diluted with 1N aqueous hydrochloric acid and evaporated under vacuum. The contents were washed down with methanol and evaporated under vacuum. The hydrochloride salt of the amine was left drying under vacuum overnight. N-carbobenzyloxy alanine (0.29 g, 1.3 mmol) was dissolved in methylene chloride followed by dicyclohexylcarbodiimide (1.0M/CH$_2$Cl$_2$; 0.65 mL) The reaction was left stirring for about 1 h at room temperature. The precipitated dicyclohexylurea was filtered off and the filtrate evaporated under vacuum. The resulting symmetrical anhydride was taken into DMF and added to the crude amine. N-methylmorpholine (54 μl, 50 mg, 0.49 mmol).was added and the reaction was left stirring at room temperature overnight. The DMF was evaporated under vacuum and the residue was dissolved in chloroform:methanol (97:3) and flash chromatographed on silica gel to give (49). $^1$H NMR (CDCl$_3$) δ7.33 (m), 6.73 (br s), 5.3–3.0 (m), 1.67–1.0 (m); MS (DCI/NH$_3$) (M+H)$^+$594.

EXAMPLE 12

Preparation of (2R)-2-(1-[(1R)-1-(N-t-butyloxycarbonylalanyl) amino-ethyl]-3-benzyl-4-hydroxy-2,3,4,5,6,7-tetrahydro-1H-azepin-5-yl)-1-oxo-propyl-valinyl-valine methyl ester (67)

Compound 67 of Scheme 6 hereabove is prepared as follows:

a.) (4R)-3-(4-methoxy) phenylacetyl-4-benzyl-2-oxazolidinone (51)

Oxalyl chloride (50 mL) is added to a solution of 4-methoxyphenylacetic acid (50 g) in dry toluene (10 mL) and the reaction is stirred at room temperature for 16 h. The reaction mixture is then evaporated to dryness and re-evaporated from toluene several times to remove any excess oxalyl chloride. The resulting crude acid chloride is next added to a solution of the lithium salt of (R)-4-benzyl-2-oxazolidinone at −78° C. (prepared from a solution of (R)-4-benzyl-2-oxazolidinone (60 g) in dry THF (700 mL) to which is added a solution of n-butyllithium (130 mL, 2.5N in n-hexane) at −78° C. with stirring for 10 min). After stirring for an additional 1 h at −78° C., the reaction is quenched with saturated NH4Cl, extracted with ethyl acetate, washed with saturated NaCl, dried over MgSO4 and evaporated. The product (51) is obtained by crystallization from ethyl acetate and n-hexane.

b.) (4R)-3-[(2R)-2-methyl-2-(4-methoxy-phenyl)-1-oxo-ethyl]-4-benzyl-2-oxazolidinone (52)

To a stirred solution of the above amide (51) in dry THF (500 mL) at −78° C. under Ar, is added a solution of lithium bis-trimethylsilylamide (1.05 equivalents, 1N in THF). After stirring for 15 min, methyl iodide (1.6 equivalents) is added in one portion. The reaction is stirred for 1 h at −78° C., then allowed to warm to 0° C. for 1 h. The reaction is then quenched with saturated NH4Cl, extracted with ethyl acetate, washed with saturated NaCl, dried over MgSO4 and evaporated. The product (52) is obtained by flash chromatography (silica gel eluted, 20% ethyl acetate/n-hexane) and is then recrystallized to remove any trace of the other diastereomer.

c.) (2R)-2-methyl-2-(4-methoxy)phenyl-ethanol (53)

The above amide (52) is dissolved in THF and treated at 0° C. with a solution of LiAlH4 in THF (1.5 equivalents). After the reaction is complete (tlc), the reaction mixture is treated with water, 3N NaOH (aqueous) and water and the residue is filtered, dried over MgSO4 and evaporated at reduced pressure. The residue is purified by flash chromatography to give the optically pure alcohol (53).

d.) methyl 4-[(1R)-1-benzyloxymethyl-ethyl]-6-oxo-hex-3-(Z)-enoate (56)

Liquid ammonia (520 mL) is condensed in a three-necked flask which was fitted with a cold finger and overhead stirrer and kept at −78° C. with a dry ice/isopropanol bath. A solution of (53) in tetrahydrofuran (140 mL) is added to the reaction flask followed by the addition of small pieces of lithium wire (4.5 equivalents) over a period of about 15 min. The reaction mixture is stirred an additional 30 min. at −78° C. and then quenched by the slow addition of absolute ethanol (400 mL). After the reaction is completely quenched (white color), it is allowed to warm to room temperature overnight. This allows most of the NH3 to evaporate. The residue is partitioned between water and diethyl ether, the organic layer collected, dried over anhydrous MgSO4, filtered and evaporated at reduced pressure. The residue, which still contains some water, is dissolved in methylene chloride, dried over anhydrous MgSO4, filtered and evaporated at reduced pressure to give crude (54) which is used in the next step without further purification.

The crude diene (54) from above is dissolved in THF and treated with NaH (1.05 equivalents, 60% in oil dispersion) at 0° C. followed by the slow addition of benzyl bromide (1.2 equivalents). The reaction is then warmed to reflux until the reaction is complete. After cooling, the reaction is treated with water and extracted with ethyl acetate. The combined organic extracts are evaporated at reduced pressure to give crude (55) which is used in the next step without further purification.

Approximately 164 mmol of crude diene (55) from above is dissolved in a mixture of methanol and dichloromethane (4:1, 500 mL), the resulting solution is cooled to −78° C. and treated with O3 until the diene disappeared by TLC. The reaction mixture is then reduced with methyl sulfide (25 mL) and slowly brought to room temperature where it is stirred for 18 h. The reaction mixture is evaporated at reduced pressure and the residue purified by flash chromatography to give pure (56).

e.) methyl 4-[(1R)-1-benzyloxymethyl-ethyl]-6-[(1R)-1-butyloxycarbonyl-ethyl]amino-hex-3-(Z)-enoate (57)

HCl.H-D-Ala-OtBu (1.5 equivalents) is dissolved in methanol and treated with NaOAc (1.5 equivalents) followed in 5 min. by the aldehyde (56) (1 equivalent) and NaBH3CN (1 equivalent). The reaction is stirred for 1 h at room temperature and then evaporated at reduced pressure. The residue is taken into ethyl acetate, washed with water, dried over MgSO4 and evaporated. The residue is purified by flash chromatography to give pure aminodiester (57).

f.) 1-[(1R)-1-butyloxycarbonyl-ethyl]-5-[(1R)-1-benzyloxymethyl-ethyl]-2,3,6,7-tetrahydro-1H-azepin-2-one (58)

The amine (57) from above (1 equivalent) is dissolved in dioxane and the resulting solution is treated with 1N NaOH (1.5 equivalents, aqueous) at room temperature for 4 h. The reaction mixture is then treated with 3N HCl (aqueous) and evaporated under high vacuum. The residue is re-evaporated from toluene (2×) and the resulting amino acid hydrochloride is dissolved in dry N,N-dimethylformamide. The resulting solution is cooled to 0° C. and is treated sequentially with triethylamine (3 equivalents), and DPPA (2 equivalents). The reaction mixture is slowly brought to room temperature (over 1 day) and then is stirred for an additional 2 days. After this time, the reaction mixture is evaporated under high vacuum and the residue purified by flash chromatography to give (58).

g) 1-[(1R)-1-butyloxycarbonyl-ethyl]-3-benzyl-5-[(1R)-1-benzyloxymethyl-ethyl]-2,3,6,7-tetrahydro-1H-azepin-2-one (59)

The intermediate (58) (1 equivalent ) is dissolved in tetrahydrofuran and cooled to −78° C. The resulting reaction mixture is treated with 1.1 equivalents of a 1M solution of lithium bis(trimethylsilyl)amide in tetrahydrofuran and is stirred for 20 min. Benzyl bromide (2 equivalents) is added, the reaction continued at −78° C. for 10 min and then warmed to 0° C. (removed dry ice/isopropanol bath). After the reaction mixture reaches 0° C., 10% NH4Cl (aqueous) is added and the resulting mixture is extracted with ethyl acetate. The combined organic fractions are dried over anhydrous MgSO4, filtered and evaporated at reduced pressure. The residue was purified using flash chromatography to give a mixture of diastereomers (59).

h.) 1-[(1R)-1-aminocarbonyl-ethyl]-3-benzyl-5-[(1R)-1-benzyloxymethyl-ethyl]-2,3,6,7-tetrahydro-1H-azepin-2-one (60)

The esters (59) are treated with TFA at room temperature for 2 h. The reaction mixture is evaporated and then evaporated from toluene (2×). The residue is dissolved in THF, cooled to −10° C. and treated with 2.5 equivalents of N-methylmorpholine and 1.5 equivalents ethyl chloroformate and stirred at −10° C. for 30 min. At this time, a solution of NH4OH in THF is added and the reaction is slowly warmed to 0° C. over 1 h. The reaction mixture is then poured into ice cold 3N HCl (aqueous) and is extracted with ethyl acetate. The combined organic extracts are evaporated at reduced pressure and the residue purified by flash chromatography to give a mixture of diastereomers (60).

i.) 1-[(1R)-1-(N-t-butyloxycarbonylalanyl)amino-ethyl]-3-benzyl-5-[(1R)-1-benzyloxymethyl-ethyl]-2,3,6,7-tetrahydro-1H-azepin-2-one (61)

The amide (60) is dissolved in CH$_3$CN/H$_2$O (4:1) and is treated with [bis(trifluoroacetoxy)iodo]benzene (1.2 equivalents) at room temperature for 4 h. The solution is evaporated at reduced pressure and then evaporated 2× from toluene. The residue is dissolved in DMF and is treated with Et$_3$N (1.2 equivalents, pH=8) followed by (Boc-Ala)$_2$O (3 equivalents) and the resulting mixture is stirred overnight at room temperature. The reaction mixture is evaporated at reduced pressure and the residue is purified by flash chromatography to give the diastereomers 61a and 61b.

j.) 1-[(1R)-1-(N-t-butyloxycarbonylalanyl)amino-ethyl]-3-benzyl-4-hydroxy-5-[(1R)-1-benzyloxymethyl-ethyl]-hexahydro-1H-azepin-2-one (62)

A single isomer of the retro peptide (61) is dissolved in THF and treated at 0° C. with thexylborane (0.5M in THF, 1.05 equivalents) and stirred at room temperature until all of (61) disappears (tlc). The reaction mixture is then treated with alkaline hydrogen peroxide to give, after extractive workup, the crude alcohol (62) as a mixture of diastereoisomers at position 4 which is then separated by column chromatography.

This reaction is repeated on the other position 3 isomer of 61 to give two additional isomers of 62.

k.) 1-[(1R)-1-(N-t-butyloxycarbonylalanyl)amino-ethyl]-3-benzyl-4-(t-butyldimethylsilyl)oxy-5-[(1R)-1-benzyloxymethyl-ethyl]-hexahydro-1H-azepin-2-one (63)

A single isomer of the alcohol (62) is dissolved in DMF and treated with imidazole (2 equivalents) and t-butyldimethylsilyl chloride (1.05 equivalents) at room temperature overnight. The reaction mixture is poured into water and extracted with ethyl acetate. The combined organic extracts are dried over MgSO$_4$ and evaporated at reduced pressure. The residue is purified by flash chromatography to give (63).

The same procedure is then repeated on the other three isomers of 62 to yield the corresponding isomers of 63.

l.) 1-[(1R)-1-(N-t-butyloxycarbonylalanyl)amino-ethyl]-3-benzyl-4-(t-butyldimethylsilyl)oxy-5-[(1R)-1-carboxy-ethyl]-2,3,4,5,6,7-tetrahydro-1H-azepin-2-one (65)

A single diastreomer of the protected alcohol (63) is dissolved in MeOH along with 5% Pd/C and is treated with H$_2$ in a Paar apparatus until H$_2$ uptake ceases. The catalysis is removed by filtration through Celite ® and the reaction mixture is evaporated to give the crude alcohol (64) which is used in the next step without further purification.

The resulting alcohol (64) is dissolved in acetone and the resulting mixture is cooled to 0° C. Jones reagent (2.5 equivalents) is added and the reaction continued for 1 h. At this time any excess Jones reagent is destroyed by the addition of isopropanol and the mixture evaporated. The residue is dissolved in ethyl acetate, washed with water dried over MgSO$_4$ and evaporated at reduced pressure. Purification by flash chromatography gives the acid (65).

The same procedure is then repeated on the three other isomers of 63 to yield the corresponding diastereomeric acids (65).

m.) (2R)-2-(1-[(1R)-1-(N-t-butyloxycarbonylalanyl)amino-ethyl]-3-benzyl-4-(t-butyldimethylsilyl)oxy-hexahydro-1H-azepin-5-yl)-1-oxo-propyl-valinyl-valine methyl ester (66)

One isomer of the acid (65) is dissolved in DMF and is treated sequentially with HCl.H-Val-Val-OMe (2 equivalents), HOBt (2 equivalents), N-methylmorpholine (6 equivalents) and Bop reagent (2 equivalents) and the reaction is stirred at room temperature overnight. The solvent is removed under vacuum and the residue purified by flash chromatography. The carboxy group is converted to Cbz-NH which is converted to Boc-Ala-NH by the procedure of Example 9.

The same procedure is then repeated on the three other isomers of 65 to yield the corresponding diastereomers of 66.

n.) (2R)-2-(1-[(1R)-1-(N-t-butyloxycarbonylalanyl)amino-ethyl]-3-benzyl-4-hydroxy-hexahydro-1H-azepin-5-yl)-1-oxo-propyl-valinyl-valine methyl ester (67)

One isomer of the protected alcohol (66) is dissolved in THF and treated with n-Bu$_4$NF (1M in THF, 2 equivalents) at room temperature. After all of the ether disappears (tlc), the reaction mixture is evaporated at reduced pressure and the residue is purified by flash chromatography to give the title compound (67).

The same procedure is then repeated on the other three isomers 66 to yield the corresponding diastereomeric products (67).

EXAMPLE 13

Preparation of
(2S)-2-(3-benzyl-4-[(1R)-1-(benzyloxycarbonyl-alanylamino)-ethyl]-5-oxo-6-benzyl-hexahydro-1H,4H-1,4-diazepin-1-yl)-3-phenyl-1-oxo-propyl-valinyl-valine methyl ester (84)

Compound 84 of Scheme 7 hereabove is prepared as follows:

a.) N-allyl-D-alanine t-butyl ester (69)

D-Alanine t-butylester (68) is treated with one equivalent allyl bromide and one equivalent of triethylamine in toluene under reflux. The solvent is evaporated and the product is purified by flash chromatography on silica gel to give (69).

b.) N-benzyloxycarbonyl-N-allyl-D-alanine t-butyl ester (70)

N-Allyl-D-alanine t-butyl ester (69) is treated with 1.1 equivalents of benzyl chloroformate and 1.1 equivalents of triethylamine in methylene chloride at room temperature overnight. After evaporation of solvent, the product is purified by silica gel chromatography to give (70).

c.) N-benzyloxycarbonyl-N-(2-oxo-ethyl)-D-alanine t-butyl ester (71)

Cbz-N-allyl-D-alanine t-butylester (70) in methylene chloride is treated with ozone at −78° C. until a blue color persists. The ozonide is quenched with dimethylsulfide and allowed to warm to room temperature. Excess dimethylsulfide is removed by bubbling a stream of nitrogen into the solution. After evaporation of solvent the product is purified by flash chromatography over silica gel to give (71).

d.) N-benzyloxycarbonyl,N-(2-(N′-[(1S)-2-phenyl-1-methoxycarbonyl-ethyl]amino)-ethyl)-D-alanine t-butylester (72)

N-Cbz-N-(2-oxo-ethyl)-D-alanine t-butylester (71) is treated with phenylalanine methyl ester and sodium cyanoborohydride in methanol buffered with sodium acetate. After evaporation of solvent the product is purified by flash chromatography over silica gel to give (72).

e.) 2,2-dimethyl-4,6-dioxo-5-benzyl-1,3-dioxane (74)

Meldrum's acid (73) is treated with benzaldehyde in the presence of borane-triethylamine complex in toluene. The product is isolated by flash chromatography over silica gel to give (74).

f.) benzyl 2-benzyl-malonate (75)

2,2-Dimethyl-4,6-dioxo-5-benzyl-1,3-dioxane (74) is refluxed with benzyl alcohol. The reaction mixture is diluted with ethyl acetate and extracted with 1N NaHCO$_3$. The aqueous extracts are acidified to pH 2.0 with solid NaHSO$_4$ and then extracted with ethyl acetate. After drying over Na$_2$SO$_4$, the ethyl acetate is evaporated and the product purified by flash chromatography over silica gel to give (75).

g.) 3-hydroxy-2-benzyl-propanoic acid (76)

benzyl 2-benzyl malonate (75) is treated with lithium aluminum hydride in THF at −78° C. The reaction is allowed to warm to room temperature and then is quenched with aqueous HCl. The reaction mixture is diluted with water and extracted with ethyl acetate. After drying over Na$_2$SO$_4$, the ethyl acetate is evaporated and the product purified by flash chromatography over silica gel to give (76).

h.) 3-(t-butyldimethylsilyl)oxy-2-benzyl-propanoic acid (77)

3-Hydroxy-2-benzyl-propionic acid (76) is treated with excess t-butyl-dimethylsilyl chloride and an equivalent amount of imidazole in dimethylformamide at room temperature overnight. After removal of solvent, the residue is dissolved in ethyl acetate and extracted with 1N NaHSO$_4$. The ethyl acetate is dried over Na$_2$SO$_4$ and evaporated to yield the crude bis-silyl ester-ether, which is purified by flash chromatography on silica gel.

The bis-silyl ester-ether is then stirred in glacial acetic acid for one hour at room temperature. After evaporation of solvent, the product is purified by flash chromatography over silica gel to give (77).

i.) benzyl 3-(t-butyldimethylsilyl)oxy-2-benzyl-propanoate (78)

3-(t-Butyldimethylsilyl)oxy-2-benzyl-propanoic acid (77) is dissolved in methylene chloride and treated with 3 equivalents each of dicyclohexylcarbodiimide, 4-(N,N-dimethylamino)pyridine and benzyl alcohol at room temperature overnight. The reaction mixture is filtered and the filtrate diluted with methylene chloride and extracted with 1N NaHCO$_3$. The organic layer is dried over Na$_2$SO$_4$, evaporated to dryness and the resulting product is purified by flash chromatography over silica gel.

j.) benzyl 3-oxo-2-benzyl-propanoate (79)

Benzyl 3-(t-butyldimethylsilyl)oxy-2-benzyl-propanoate (78) is treated with tetrabutylammonium fluoride in methylene chloride for one hour at room temperature. The reaction mixture is washed 1N NaHSO$_4$ with and water, then dried over Na$_2$SO$_4$.

The resulting crude alcohol is dissolved in dry dimethylsulfoxide and treated with 3 equivalents of triethylamine and 3 equivalents of pyridine.SO$_3$ complex at room temperature for 10 min. The reaction mixture is poured into cold water, extracted with ether and the ether layers washed with 1N NaHSO$_4$, water and 1N NaHCO$_3$, dried over Na$_2$SO$_4$. Evaporation of solvent affords the crude aldehyde (79) which is used without further purification.

k.) N-benzyloxycarbonyl, N-(2-(N′-[2-benzyloxycarbonyl-3-phenyl-propyl], N′-[(1S)-2-phenyl-1-methoxycarbonyl-ethyl])amino)-ethyl-D-alanine t-butyl ester (80)

Compounds (72) and (79) are dissolved in methanol buffered with sodium acetate and are treated with sodium cyanoborohydride at room temperature overnight. The product (80) is obtained by evaporation of the solvent and purification by flash chromatography over silica gel.

l.) 6-benzyl-4-[(1R)-1-t-butyloxycarbonyl-ethyl]-1-[(1S)-1-methoxycarbonyl-2-phenyl-ethyl]-hexahydro-1H, 4H-1,4-diazepin-5-one (81)

Compound (80) is hydrogenated over 10% Pd on carbon in methanol. The catalyst is filtered off through a pad of Celite ® and the filtrate is evaporated to dryness to yield the crude free amine acid.

The amine acid is dissolved in dimethylformamide and treated with 1.1 equivalents of diphenylphosphoryl azide and 1.1 equivalents of triethylamine at 4° C. for three days. Evaporation of the solvent and purification by flash chromatography over silica gel afford the pure cyclized product (81).

m.) 6-benzyl-4-[(1R)-1-(benzyloxycarbonyl)aminoethyl]-1-[(1S)-1-methoxycarbonyl-2-phenyl-ethyl]-hexahydro-1H,4H-1,4-diazepin-5-one (82)

Compound (81) is treated with 50% trifluoroacetic acid in methylene chloride at room temperature for 1 h. Evaporation of the solvent followed by evaporation of the residue from methylene chloride three times affords the crude free acid.

The free acid is dissolved in toluene and refluxed in the presence of diphenylphosphoryl azide and benzyl alcohol overnight. After evaporation of the solvent, purification by flash chromatography over silica gel affords compound (82).

n.) (2S)-2-(3-benzyl-4-[(1R)-1-(benzyloxycarbonylamino)-ethyl]-5-oxo-6-benzyl-hexahydro-1H, 4H-1,4-diazepin-1-yl)-3-phenyl-1-oxo-propyl-valinyl-valine methyl ester (83)

The methyl ester group of compound (82) is saponified with base followed by coupling to Val-Val-OMe using BOP (benzotriazol-1-yloxy-tris (dimethylamino) phosphonium hexafluorophosphate), N-methylmorpholine (NMM) and 1-hydroxy-benzotriazole (HOBt) to give the title compound.

o.) (2S)-2-(3-benzyl-4-[(1R)-1-(benzyloxycarbonylalanylamino)-ethyl]-5-oxo-6-benzyl-hexahydro-1H, 4H-1,4diazepin-1-yl)-3-phenyl-1-oxo-propyl-valinyl-valine methyl ester (84)

The benzyloxycarbonyl group is removed by catalytic hydrogenation, then the resulting amino group is coupled to Cbz-Ala using BOP, HOBt and NMM to give the title compound.

The benzyloxycarbonyl group (Cbz) is removed by catalytic hydrogenation to give (2S)-2-(1H,4H-3-benzyl-4-[(1R)-1-(alanylamino)-ethyl]-5-oxo-6-benzyl-hexahydro1H,4H-1,4-diazepin-1-yl)-3-phenyl-1-oxo-propyl-valinyl-valine methyl ester (85).

EXAMPLE 14

Liposomal Dosage Unit Composition

Phosphatidylcholine (1.4 g) and phosphatidylglycerol (0.6 g) are dissolved in 300 ml of a 20% methanol in chloroform solvent and evaporated to dryness. A solution of the compound of Example 2 (30 mg in 200 ml of phosphate buffered saline) is added to the dry phospholipid film which is allowed to equilibrate at room temperature for 1-2 hr. The liposome dispersion formed is then vortexed to insure uniform mixing. The resulting suspension is extruded through a 0.2μ polycarbonate filter five times to produce a uniform size distribution. If necessary, the suspension can be dialysed or ultracentrifuged to remove non-encapsulated compound.

EXAMPLE 15

Liposomal Dosage Unit Composition

In a beaker, cholesterol (49 mg) and oleic acid (0.358 g) are warmed to 65° C. for 20-30 min. Maintaining the temperature, phospholipids (1 g) are added slowly, ensuring complete wetting by the oleic acid. A solution of arginine (0.22 g in 3.37 g water) at 40° C. is added in small aliquots and thoroughly mixed into the slurry. Mixing is maintained at 40° C. After equilibration for one week, the compound of Example 8 (150 mg) is mixed thoroughly into the gel. The pH is adjusted to 7.0 with acetic acid if necessary. Phosphate buffered saline (pH 7.4) is added in small aliquots with vortexing to achieve a concentration of 200 mg of liposomal gel per mL. Liposomes form spontaneously. This procedure produces 5 g of liposomal suspension. A standard dosage unit is 1 g of liposomal suspension.

EXAMPLE 16

Parenteral Dosage Unit Composition

A preparation which contains 25 mg of a compound of this invention is prepared as follows: 25 mg of the compound is dissolved in 15 ml of distilled water. The solution is filtered under sterile conditions into a 25 mL multi-dose ampoule and lyophilized. The powder is reconstituted by addition of 20 mL of 5% dextrose in water (D5W) for intravenous or intramuscular injection. The dosage is thereby determined by the injection volume. This solution is also suitable for use in other methods for administration, such as addition to a bottle or bag for IV drip infusion.

EXAMPLE 17

Oral Dosage Unit Composition

A capsule for oral administration is prepared by mixing and milling 35 mg of the compound of Example 8 with 75 mg of lactose and 5 mg of magnesium stearate. The resulting powder is screened and filled into a hard gelatin capsule.

What is claimed is:

1. A compound of the formula:

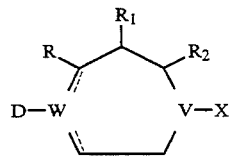

in which:

D is A' or

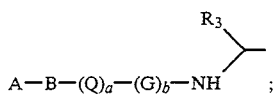

X is

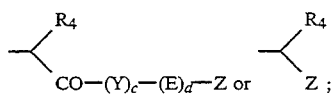

V and W are each independently N or C;

one of -- indicated bonds is a double bond and the other is a single bond or, when W is N, -- both are single bonds;

R is hydrogen or OH, or when W is N, R is =O;

$R_1$ is $C_{1-6}$ alkyl, $(CH_2)_n$ Ar, $(CH_2)_n$ Het, $(CH_2)_n CONHR'$, $(CH_2)_n OR'$ or $(CH_2)_n SR'$;

$R_2$ is:

a) 2H, when V is N;

b) OH, OR', =CHR' or NHR', when c) =O, when W and V are both N;

A' is hydrogen, $C_{1-6}$ alkyl, benzyl, halobenzyl, dihalobenzyl or tosyl;

A is hydrogen or an amino protecting group;

B is a D or L amino acid or is a covalent bond;

Q is a D or L amino acid selected for Ser, Thr, Asp, His, Cys, Arg and Ala;

G is Glx, Asx, Ala, β-Ala, Arg, Gly, Ile, Leu, Lys, Ser, Thr, Val, Met or His;

Y and E are each independently a D or L amino acid;

a, b, c and d are each independently 0 or 1;

Z is hydrogen $(CH_2)_n OR'$, $(CH_2)_n NHR'$, $C_{1-6}$alkyl, $(CH_2)_n SR'$, $O(CH_2)_p OR'$, $NH(CH_2)_p OR'$, $O(CH_2)_p SR'$ or $NH(CH_2)_p SR'$;

$R_3$ and $R_4$ are each independently hydrogen, $C_{1-6}$alkyl, $(CH_2)_n$Het, $(CH_2)_n$Ar, $(CH_2)_n CONHR'$, $(CH_2)_n OR'$, $(CH_2)_n SR'$, $(CH_2)_n NHR'$, $CH(OH)CH_3$ or $(CH_2)_3 NHC(=NH)NH_2$;

R' is hydrogen, $C_{1-4}$alkyl or benzyl;

n is 0 to 3;

p is 1 to 3;

Het is indolyl or imidazolyl, or pyridyl or thienyl optionally substituted by one or two $C_{1-4}$alkyl, OR' or SR'; and Ar is phenyl optionally substituted by one or two $C_{1-4}$alkyl, OR', $NO_2$, $NH_2$, halogen, $CF_3$ or SR'; or a pharmaceutically acceptable salt thereof.

2. A compound of claim 1 in which the amino protecting group in A is t-butyloxycarbonyl, benzyloxycarbonyl, p-chlorobenzyloxycarbonyl, 2,4-dichlorobenzyloxycarbonyl, alkanoyl or tosyl.

3. A compound of claim 1 in which the amino acid in B is Ala, β-Ala, Gly, Ile, Val, Leu, Met, His, Lys, Arg, Glx, Asx, Cys, Ser or Thr.

4. A compound of claim 3 in in which at least one of Y and E is an amino acid, the same or different, selected from Ala, Gly, Ile, Leu, Met, Val, Arg, Lys, Thr, Ser, Cys, Glx and Asx.

5. A compound of claim 1 which is represented by the formula:

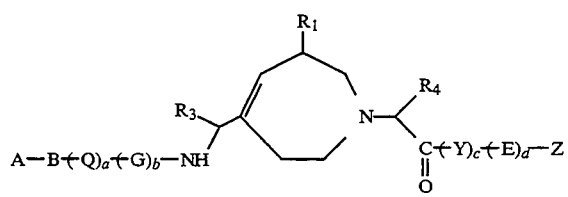

in which $R_1$, A, B, Q, G, Y, E, a, b, c, d, $R_3$, $R_4$ and Z are as defined in claim 1.

6. A compound of claim 1 which is represented by the formula:

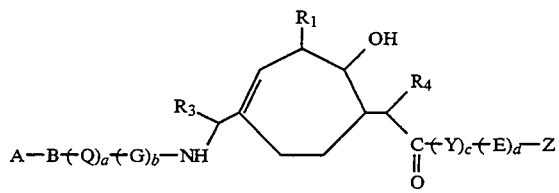

in which $R_1$, A, B, Q, G, Y, E, a, b, c, d, $R_3$, $R_4$ and Z are as defined in claim 1.

7. A compound of claim 1 which is represented by the formula:

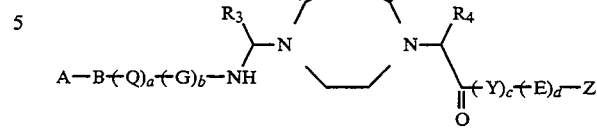

in which $R_2$ is 2H or =O; and $R_1$, A, B, Q, G, Y, E, a, b, c, d, $R_3$, $R_4$ and Z are as defined in claim 1.

8. A compound of claim 1 which is represented by the formula:

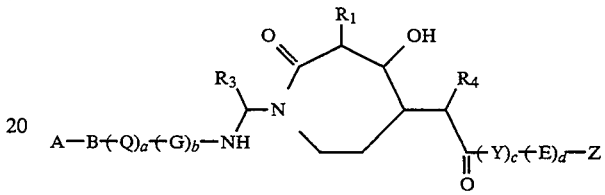

in which $R_1$, A, B, Q, G, Y, E, a, b, c, d, $R_3$, $R_4$ and Z are as defined in claim 1.

9. A compound of claim 5 which is 2-[3-benzyl-5-(1-alanylamino-ethyl)-2,3,6,7-tetrahydro-1H-azepin-1-yl]-1-oxo-propyl-valinyl-valine methyl ester.

10. A compound of claim 6 which is 2-(5-[(1S)-1-alanylamino-ethyl]-3-benzyl-2-hydroxy-cyclohept-4-en-1-yl)-1-oxo-ethyl-valinyl-valine methyl ester.

* * * * *